US012625129B2

(12) United States Patent
Ho et al.

(10) Patent No.: US 12,625,129 B2
(45) Date of Patent: May 12, 2026

(54) SYSTEMS AND METHODS FOR INERTIAL-KINETIC CAPTURE AND SENSING OF SINGLE MOLECULES

(71) Applicant: The Chinese University of Hong Kong, Hong Kong (CN)

(72) Inventors: Ho-Pui Ho, Hong Kong (CN); Jianxin Yang, Hong Kong (CN); Wu Yuan, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 147 days.

(21) Appl. No.: 18/477,768

(22) Filed: Sep. 29, 2023

(65) Prior Publication Data

US 2025/0110109 A1      Apr. 3, 2025

(51) Int. Cl.
*G01N 33/487* (2006.01)
*B82Y 15/00* (2011.01)
*G01N 27/327* (2006.01)

(52) U.S. Cl.
CPC ........ *G01N 33/48721* (2013.01); *B82Y 15/00* (2013.01); *G01N 27/3278* (2013.01)

(58) Field of Classification Search
None
See application file for complete search history.

(56) References Cited

U.S. PATENT DOCUMENTS

2012/0171087 A1 *   7/2012   Gaborski   ..........   B01D 67/0088
                                                        210/500.21

FOREIGN PATENT DOCUMENTS

| | | |
|---|---|---|
| CN | 112746006 A | 5/2021 |
| WO | 2018/236673 A1 | 12/2018 |
| WO | 2020/241752 A1 | 12/2020 |
| WO | 2021/055338 A1 | 3/2021 |
| WO | 2021/223627 A1 | 11/2021 |
| WO | 2022/060691 A1 | 3/2022 |

OTHER PUBLICATIONS

International Search Report dated Jun. 28, 2024 in International Application No. PCT/CN2023/137773.

* cited by examiner

*Primary Examiner* — J. Christopher Ball
(74) *Attorney, Agent, or Firm* — SALIWANCHIK, LLOYD & EISENSCHENK

(57) ABSTRACT

The subject invention pertains to a nanopore sensing device for inertial-kinetic translocation and sensing of single molecules. Some embodiments comprise a centrifuge rotor; a centrifuge tube; single or multiple flow cell modules; a nanopore module consisting of single or multiple nanopores; a signal detection module; a signal amplifier module; a control module; and a wireless communication module. Through the kinetic regulation of a centrifugal force field while maintaining a counter-balanced state of electrophoretic and electroosmotic forces in the nanopore by adjusting the pH value of the electrolyte in nanopore or the surface charge excited on the silicon nanopore using visible light, the precise regulation of molecular translocation parameters, such as speed, direction, and molecular selectivity, is provided for optimizing the temporal and spatial resolutions of molecular sensing with high S/N ratio signal readout.

17 Claims, 37 Drawing Sheets

2000 rpm

4000 rpm

2000 rpm

4000 rpm

SYSTEMS AND METHODS FOR INERTIAL-KINETIC CAPTURE AND SENSING OF SINGLE MOLECULES

TECHNICAL FIELD OF THE INVENTION

The invention relates to high sensitivity measurement devices. More particularly the invention relates to improved systems and methods of nanopore sensing.

BACKGROUND OF THE INVENTION

When a stream of molecules drift through a nanometer-size pore (also known as nanopore) driven by a potential difference imposed across the nanopore, the ionic channel is temporally blocked and resultant sensing signals (in terms of current, voltage, resistance, conductance) are generated [ACS Chem. Biol. 2012, 7, 1935-1949; Phys. Chem. Chem. Phys., 2022, 24, 19948-19955]. Nanopore sensing is a technique realised by measuring the sensing signals with electrodes across the nanopore [Nat. Nanotech. 12, 360-367 (2017); Nat. Nanotech. 17, 708-713 (2022); Nat. Nanotech. 17, 976-983 (2022); Nature Reviews Materials 2020, 5 (12), 931-951]. This technique can be integrated into portable sensing devices with electronics [K. Chuah, et al. Nature Communications 2019, 10, 2109]. Indeed, the so-called nanopore sequencing technique has made significant contributions in many branches of life sciences in the last two decades [N. S. Galenkamp, et al. Nature Communications, 9, 4085 (2018); Bayley, H. Nanopore sequencing: from imagination to reality. Clin. Chem. 61, 25-31 (2015).]

In principle, a nanopore of appropriate structural dimension can resolve the sizes and configurations of the molecules in question [Phys. Life rev. 9, 125-158 (2012).]. Electrokinetic translocation of a single molecule is commonly utilized in nanopore, and the speed of translocation is determined by the electrophoretic force and the viscous drag of the molecules in the solution and the pore. However, the translocation speed of molecules is challenging to control in nanopore, leading to the sensing signals of short dwell time and low conformation sensitivity. High translocation speed and low conformation sensitivity on signal readings have limited the accuracy of nanopore in molecular discrimination [Adv. Mater. 2018, 30, 1704680; Venkatesan, B. M. & Bashir, R. Nanopore sensors for nucleic acid analysis. Nat. Nanotechnol. 6, 615-624 (2011)].

Although speed control with protein motors has been successfully demonstrated with biological nanopores, it remains challenging to achieve a stable feed rate of the protein motor and a high conductance drop as in solid-state nanopores [Fragasso, ACS nano, 2020, Brinkerhoff, Science 2021]. On the other hand, a nanopositioner has been utilized to achieve controlled translocation in glass nanopore. However, this method requires tethered molecules, inhibiting them from fully translocating [Leitao Nat Nanotec 2023].

BRIEF SUMMARY OF THE INVENTION

Embodiments of the subject invention provide systems and methods to drive nano-sized objects through a nanopore by centrifugation, so that the molecules under investigation experience inertial-kinetic controlled translocation and regulated dwell time in nanopore with high conformation sensitive signal readouts. The use of inertial forces generated by centrifugation has effectively decoupled the single-molecule translocation process from experimental parameters (such as ionic strength and bias voltage) and signal detection process which use the same pair of electrodes applying bias voltage crossing the nanopore. In certain embodiments the electrophoretic and electroosmotic forces are effectively counter balanced by adjusting the pH value of the electrolyte in nanopore or the surface charge excited on the silicon nanopore with using light, while the electric field still covers the nanopore as an independent sensing method.

While electrokinetic translocation commonly results in high and uncontrolled translocation speeds of single molecules in nanopore and non-uniform conductance signals of low conformation sensitivity and short dwell time from micro- to milli-seconds [Tang, L. et al. Nat. Commun. 12, 913 (2021).], the inertia-kinetic translocation can effectively control the speed and direction of single-molecule translocation, leading to an unform sensing readouts of high conformation sensitivity and long dwell time up to hundreds of milli-seconds and a capability of programmable and selective sensing of single molecules from the complex made of multiple molecules. In addition, the inertia-kinetic translocation can help realize the reversible sensing and selective translocation of single molecules, achieving repetitive and addressable sensing of molecules with high spatial and temporal resolution. Therefore, a sensing signal, including its signal-to-noise ratio and dwell time, can be optimized by independently controlling the centrifugal force in nanopore to achieve a highly distinguishable molecular fingerprint of single molecule with improved detection limit.

Embodiments provide a centrifuge tube like in-tube nanopore sensing device, which can be conveniently placed in the centrifuge machine to achieve an inertial-kinetic nanopore sensing system. Such in-tube nanopore device basically consists of one nanopore for sensing or multiple nanopores for multiplexed sensing, one flow cell module for sample loading for each nanopore, one signal detection module for each nanopore, one signal amplifier module for each nanopore, one or multiple control modules, and one or multiple wireless communication modules, which wirelessly transmit sensing signals and enable real-time sensing of single molecules.

According to an embodiment of the invention, the inertial-kinetic nanopore sensing system of the invention further comprises one or multiple data processing modules for recording and analyzing the detected signals of single molecules.

BRIEF DESCRIPTION OF THE DRAWINGS

In FIG. 3D, $f_{CO}$, $f_{anti}$, and $f_{GFP}$ are the electrophoretic effect exerted on three example molecules: green fluorescence proteins (GFP)-antibody conjugates, antibody, and GFP, respectively.

FIG. 4A illustrates relationships between Detail FIGS. 4B-4G, including common size (10 nm), amperage (600 pA), and time (10 ms) scale bars. β represents the length-to-diameter ratio of the molecule (i.e., r/R), where r and R are the polar and equatorial semi-axis of a molecule, respectively. the time ratio (α) is calculated as $t_1/t_2$. FIGS. 4B-4G are enlarged to show details.

FIG. 8A illustrates relationships between Detail FIGS. 8B and C, including amperage (100 pA), and time (0.15 s) scale bars.

FIGS. 9B-9D are the counter-balanced state of conjugates, antibody, and GFP, respectively, in which electrokinetic forces trend towards 0. FIG. 9A illustrates the selective translocation events that were controlled by adjusting the power of illumination.

US 12,625,129 B2

Figure 1A:
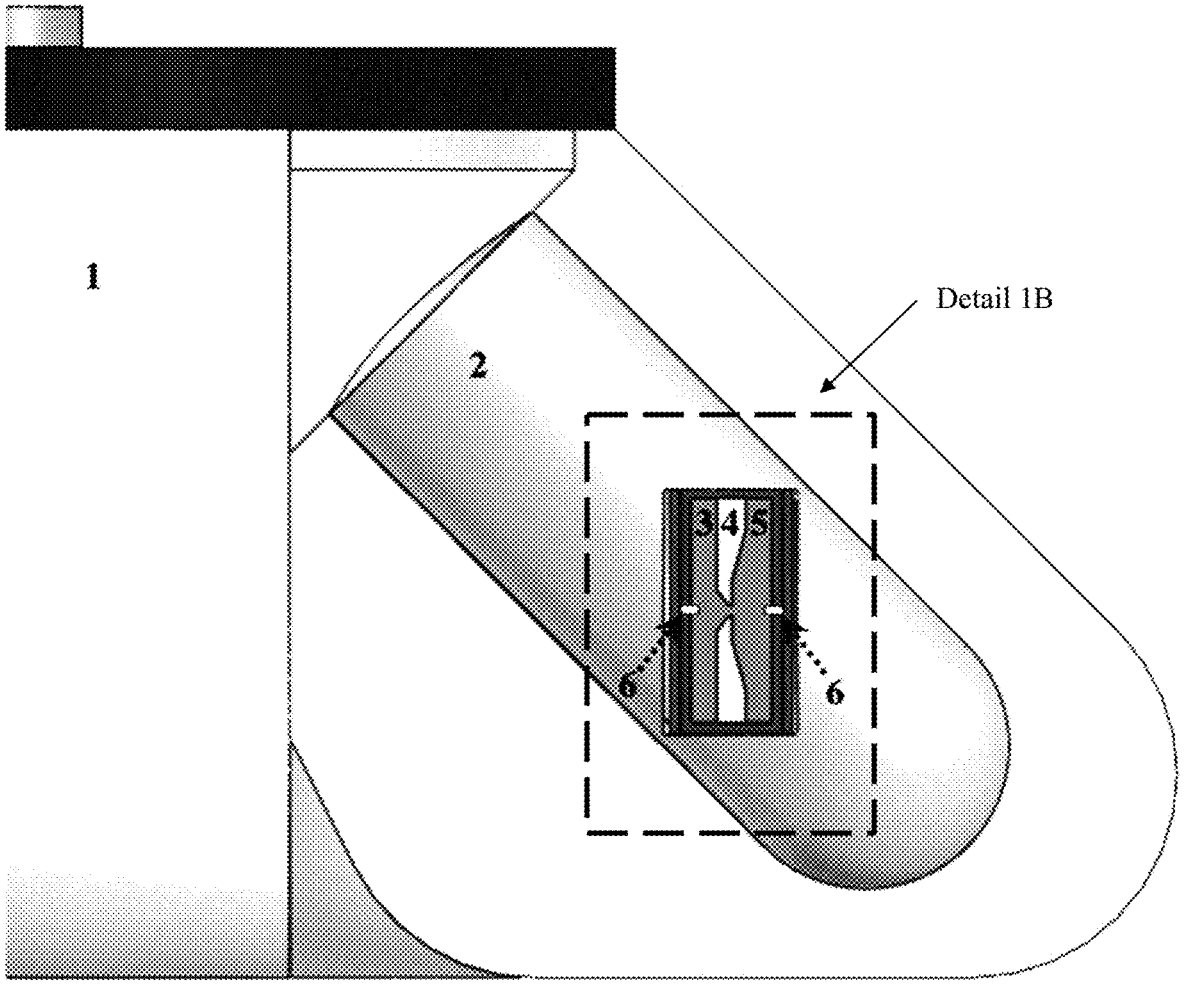
FIG. 1A is a schematic of an in-tube nanopore sensing device in a centrifuge with a nanopore module consisting of single nanopore in one flow cell module and one signal detection module using applied bias voltage to measure signals (e.g., in terms of current, voltage, resistance, and/or conductance) according to an embodiment of the subject invention.

5 out of the nanopore by reversibly changing the force direction between forward and reverse (iii, iv and v). $f_c$ is the centrifugal force exerted on antibody and $f_{eo\_peg}$ are the and electrophoretic effect exerted on EPG.

It should be understood that the examples and factors described in the figures are for illustrative purposes only and embodiments are not limited to sense these molecules with the specific factors. One of skill in the art will readily recognize broad areas of applicability including but not limited to "Small Molecules", "Chain Molecules", and "a complex of molecules".

DETAILED DISCLOSURE OF THE INVENTION

Embodiments provide a nanopore sensing device for inertial-kinetic translocation and sensing of single molecules. Certain embodiments comprise a centrifuge rotor; a centrifuge tube; single or multiple flow cell modules; a nanopore module consisting of single or multiple nanopores; a signal detection module; a signal amplifier module; a control module; and a wireless communication module. Through the kinetic regulation of a centrifugal force field while maintaining a counter-balanced state of electrophoretic and electroosmotic forces in the nanopore by adjusting the pH value of the electrolyte in nanopore or the surface charge excited on the silicon nanopore using visible light, the precise regulation of molecular translocation parameters, such as speed, direction, and molecular selectivity, is provided for optimizing the temporal and spatial resolutions of molecular sensing with high S/N ratio signal readout. Thus, the conformational sensitivity of chain- and particle-like molecules has been determined by the programmable translocation parameters. The discrimination of molecular conformation and the longitudinal monitoring of the morphological changes have been demonstrated by quantifying the dwell time and measuring the characteristic features in sensing signal traces using the provided inertial-force actuated in-tube nanopore device. In addition, the programmable translocation and selective identification of single molecules from the complex made of multiple molecules improved quantification on single molecular shape factor.

To achieve more precise molecule sensing and more accurate molecular actuation, embodiments of the subject invention provide a new single molecular sensing device incorporating an inertial-force kinetically actuated single-molecule translocation method into an in-tube nanopore system, as shown in an exemplary and non-limiting example in FIGS. 1A-1E. Embodiments comprise a centrifuge tube with a single nanopore inside a single flow cell module or multiple nanopores inside multiple flow cell modules in parallel (e.g., see FIGS. 1A-1D). Each signal detection module can apply voltage bias to the nanopore and measure the sensing signals (e.g., see FIG. 1E). In certain embodiments the measured signals are first amplified at a sensitivity of at least −1.081 V/nA using a signal amplifier module, which is cascaded to a differential circuit with low circuit noise of at most 0.4 pA (e.g., in root mean square at a sampling rate of 50 kHz). The amplified sensing signals are then digitized using a control module at a sampling rate of at least 50 kHz before being wirelessly transmitted to an external receiver via an in-tube wireless communication module at a baud rate of 115200 bits/sec.

Embodiments have also measured multi-molecule translocation signals. A novel silicon nanopore fabrication is also an integral part of certain embodiments. Embodiments of the inertial-kinetic molecular translocation method can be applied to many kinds of nanopores without outside limitation on the nanopore type.

As shown in FIGS. 2A-2D, in certain embodiments the sensor provides an extended molecular translocation time inside the nanopore on the order of milliseconds, capable of accurate molecular fingerprinting via measuring the microsecond-resolution sensing signals received by wireless communications. Embodiments can precisely describe the molecular structure by reading the sensing signal. In addition, the provided nanopore device and/or method offers an adjustable dwell time on demand by kinetically regulating a centrifugal force while maintaining the electrophoretic and electroosmotic forces in a counter-balanced state in the nanopore.

Figures 2A, 2B:
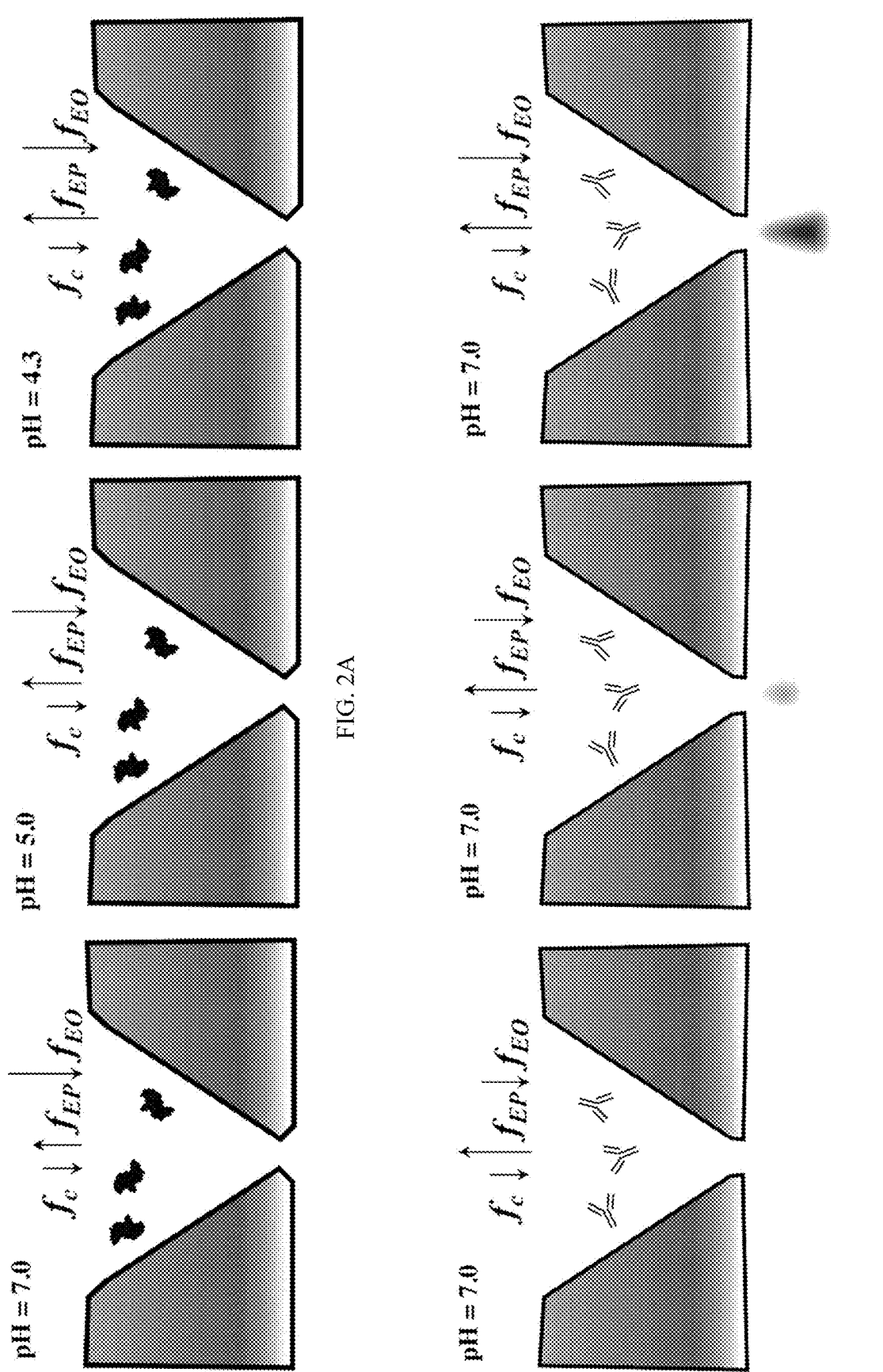
FIG. 2A is a schematic illustration of force analysis of the tested molecules at different pH value according to an embodiment of the subject invention. The external force exerted on the target molecules (i.e., bovine serum albumin, or BSA) is dominated by electrophoretic effect $f_{EP}$, electroosmosis effect $f_{EO}$, and centrifugal force $f_c$. Adjustment of pH value is able to turn the electrophoretic effect $f_{EP}$ and electroosmosis effect $f_{EO}$ to achieve a counterbalanced electrophoretic and electroosmosis effects, i.e., $f_{EP}=f_{EO}$.
FIG. 2B is a schematic illustration of force analysis of the tested molecule when the nanopore is illuminated with different optical powers according to an embodiment of the subject invention. The external force exerted on the target molecules (i.e., antibody) is dominated by $f_{EP}$, $f_{EO}$, and $f_c$. Adjustment of optical power can help achieve counterbalanced electrophoretic and electroosmosis effects, i.e., $f_{EP}=f_{EO}$.
Figure 2C:
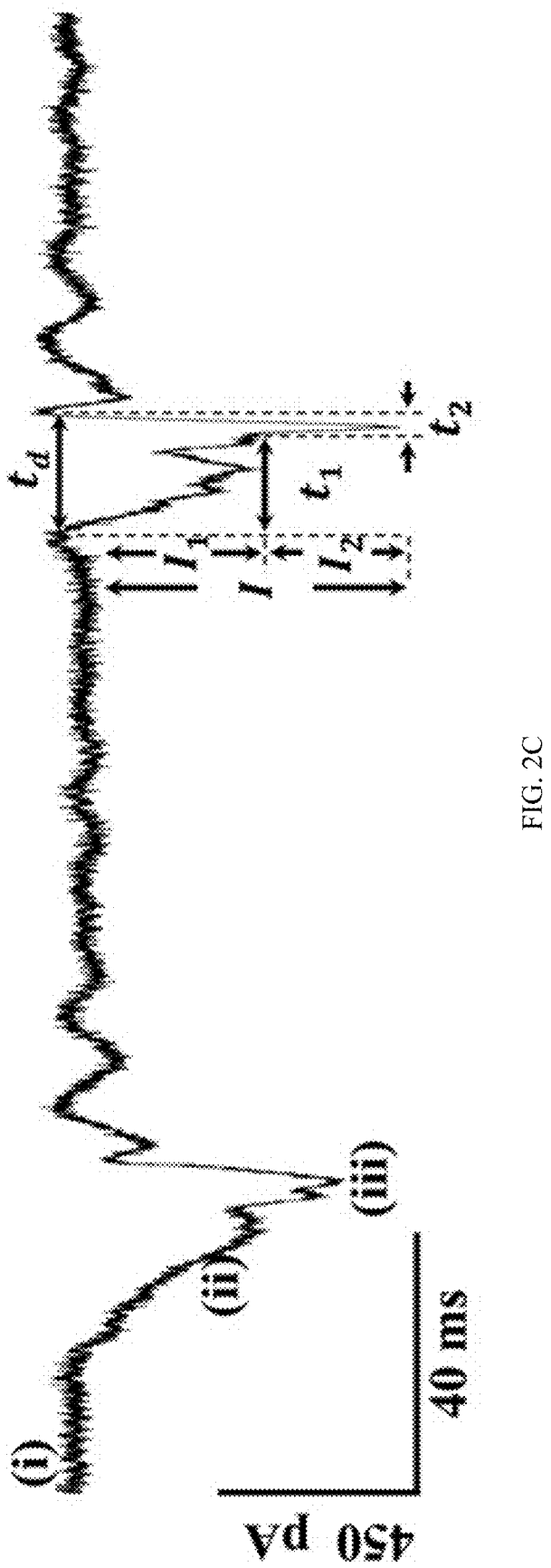
FIG. 2C shows a series of pulse-shape sensing signals received by wireless communication according to an embodiment of the subject invention. The first current drop and duration ($I_1$, $t_1$) associated with molecular capture in stage (ii), and the second current drop and duration ($I_2$, $t_2$) due to molecular translocation in stage (iii). The amplitude of current blockage I is defined as $I_1+I_2$ and the dwell time $t_d$ is calculated as $t_1+t_2$.
Figure 2D:
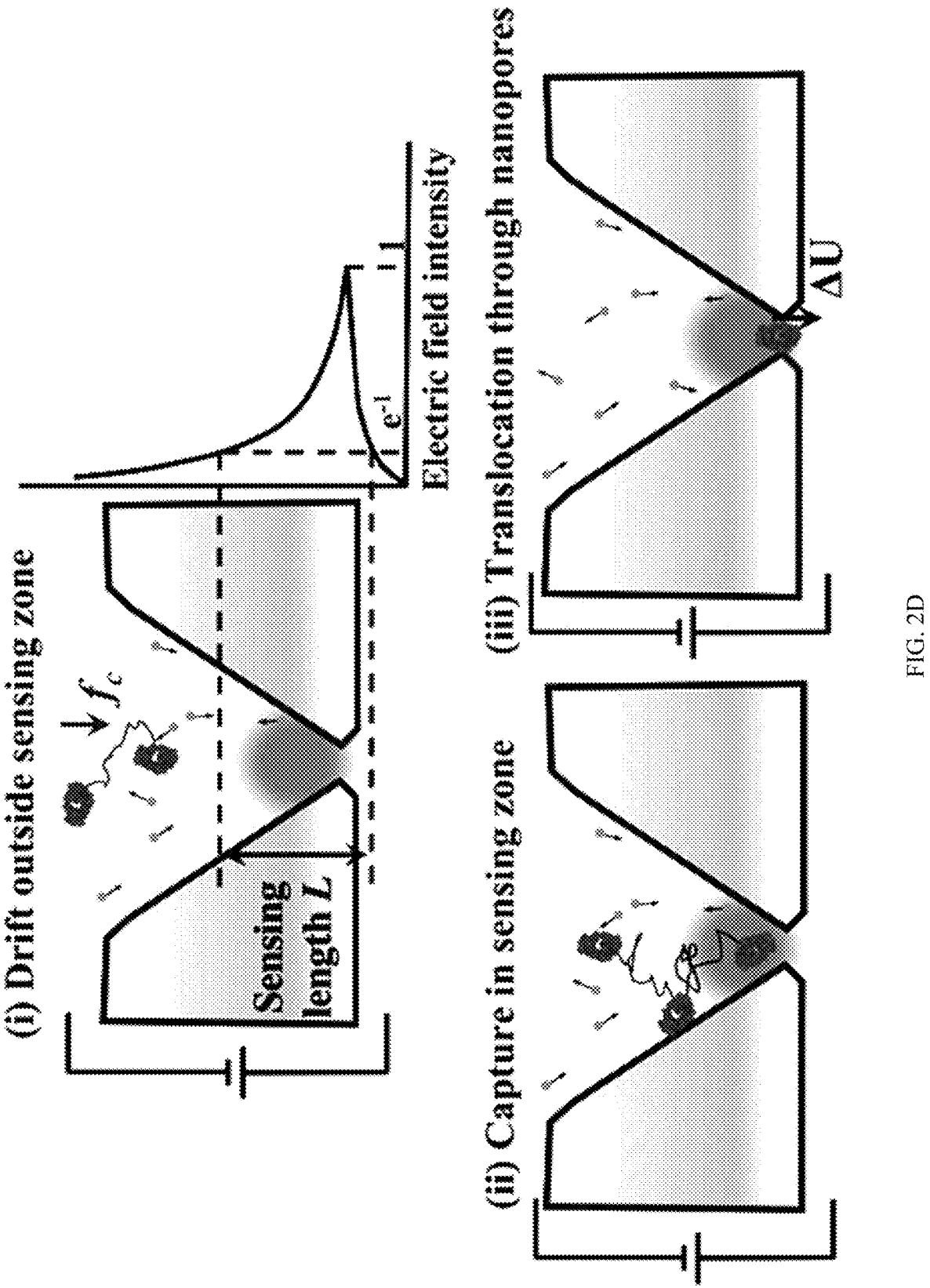
FIG. 2D is a schematic illustration of different stages of molecular motions through a nanopore according to an embodiment of the subject invention.
Figure 3A:
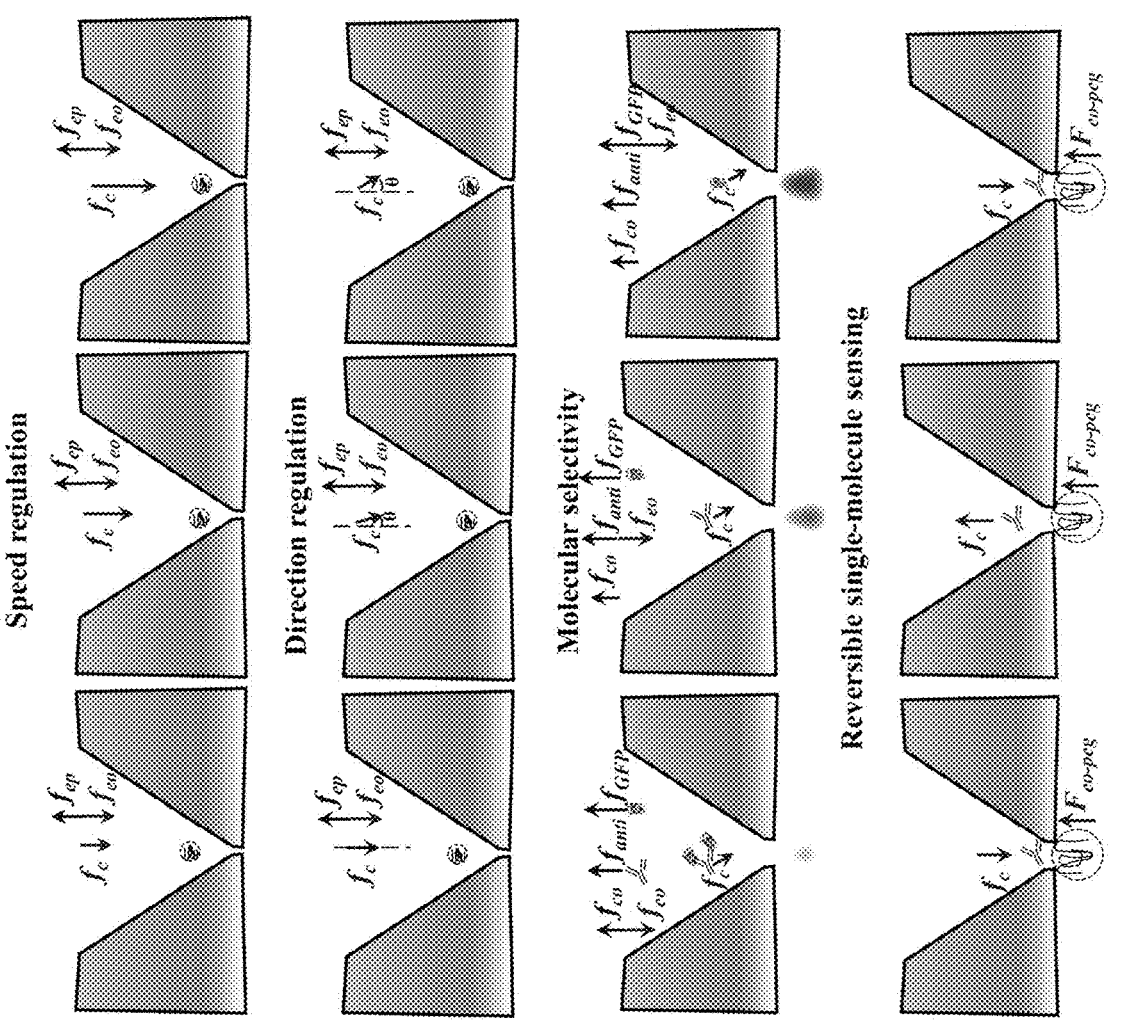
FIGS. 3A-3E are schematic illustrations of precisely regulating molecular translocation parameters, including speed (FIG. 3B), direction (FIG. 3C), molecular selectivity (FIG. 3D), and reversible single-molecule sensing (FIG. 3E) according to an embodiment of the subject invention. The external force exerted on the target molecules is dominated by electrophoretic effect $f_{EP}$, electroosmosis effect $f_{EO}$, and centrifugal force $f_c$.
Figure 3B:
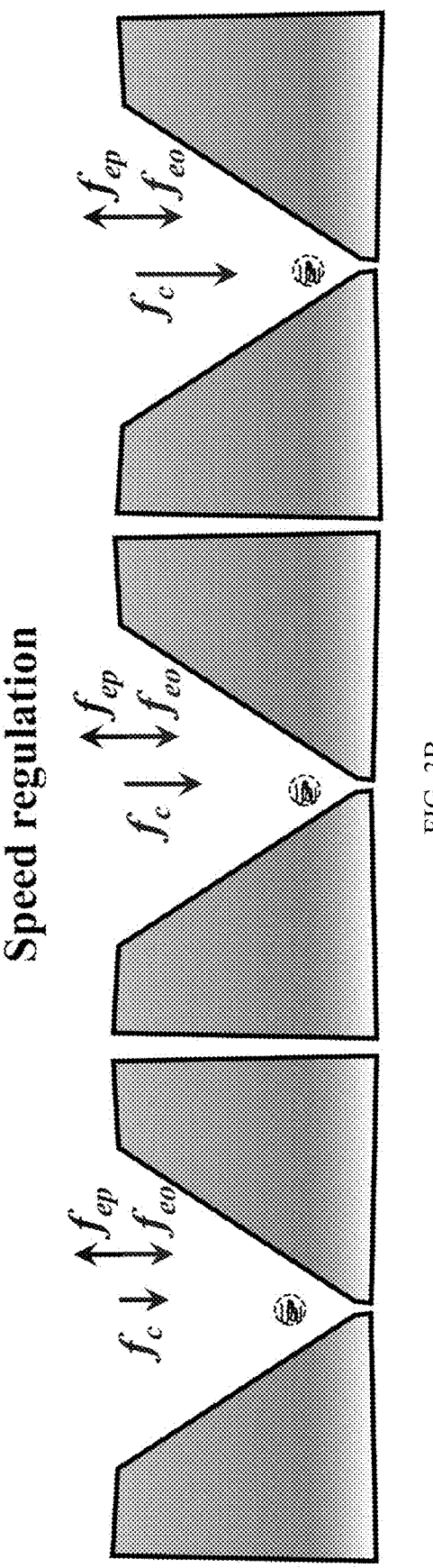
Figure 3C:
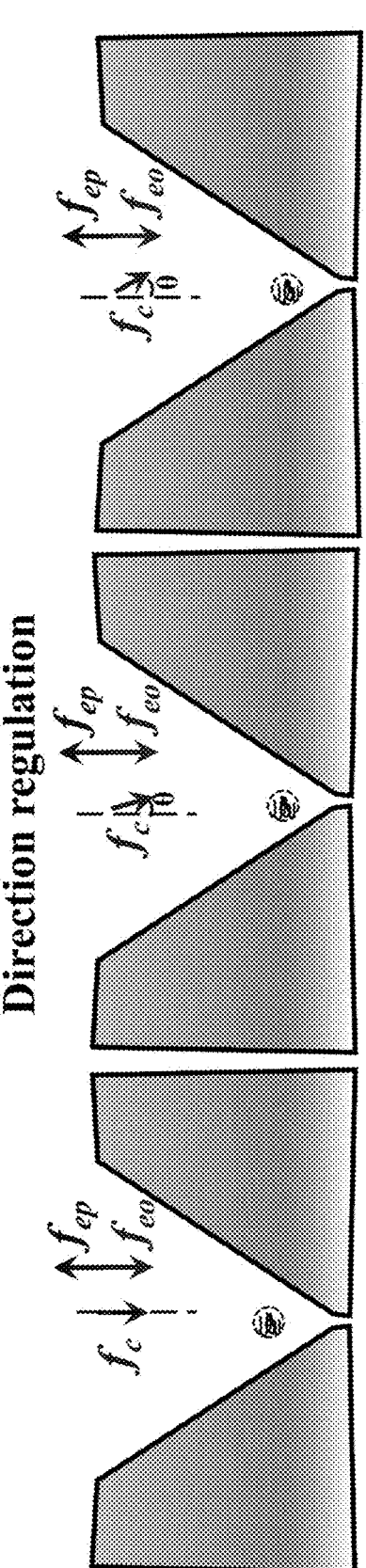
Figure 3D:
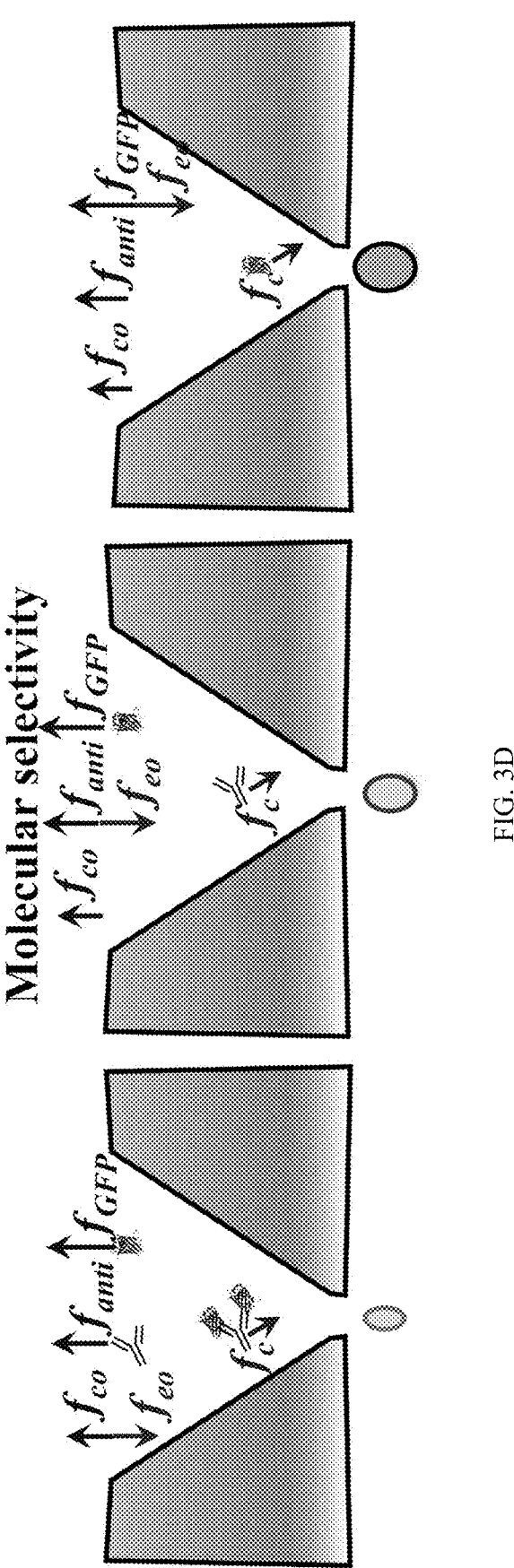
Figure 3E:
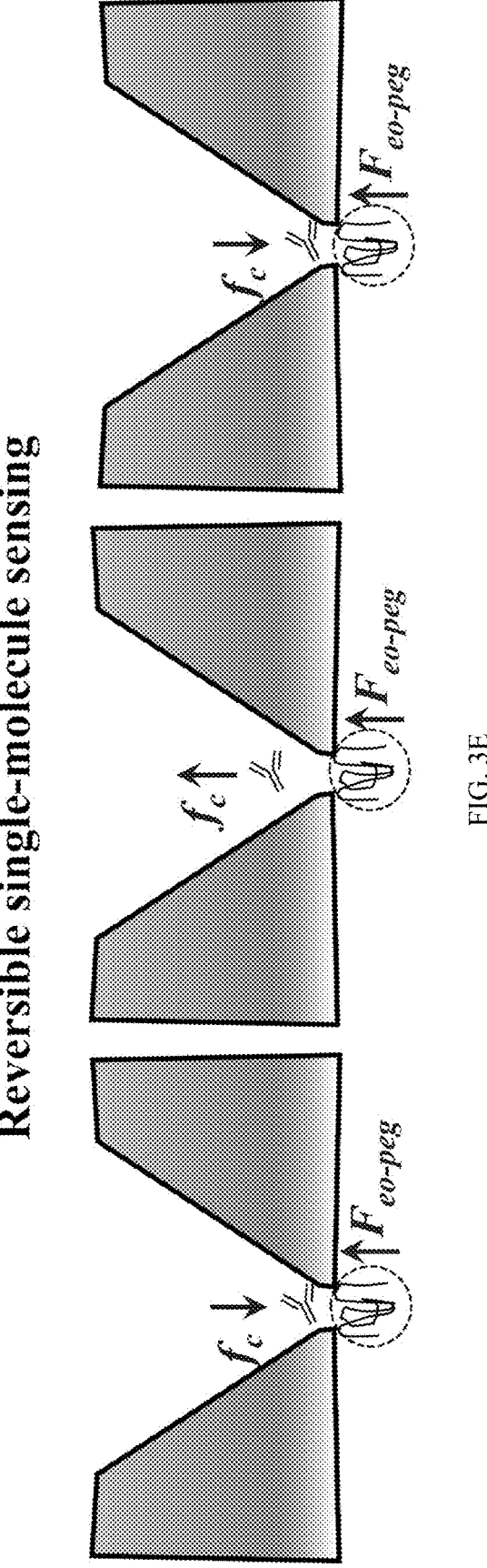
Figure 4A:
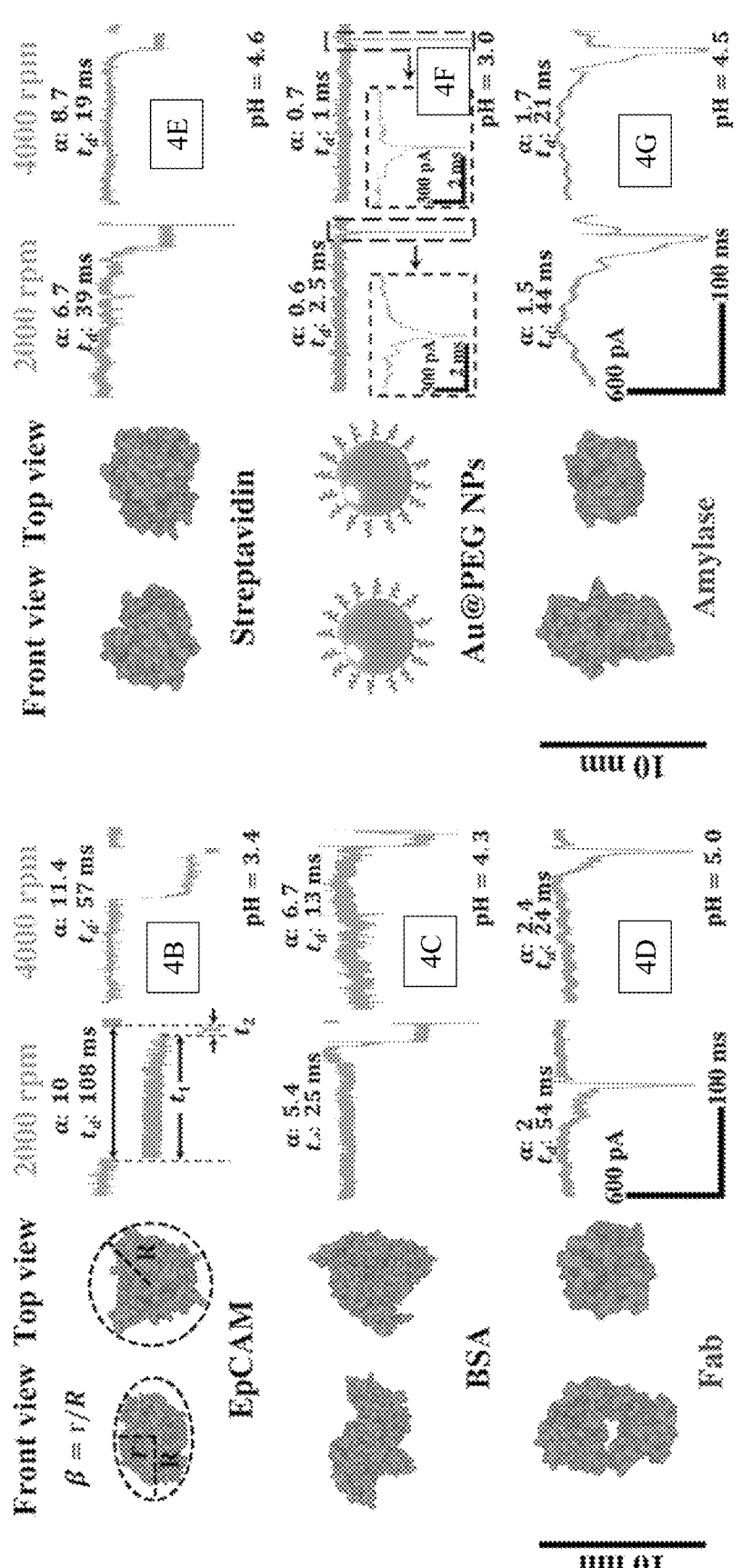
FIGS. 4A-4G show sensing signals of six example molecules measured at respective pH values of their balanced states under different rotation speeds according to an embodiment of the subject invention.
Figure 4B:
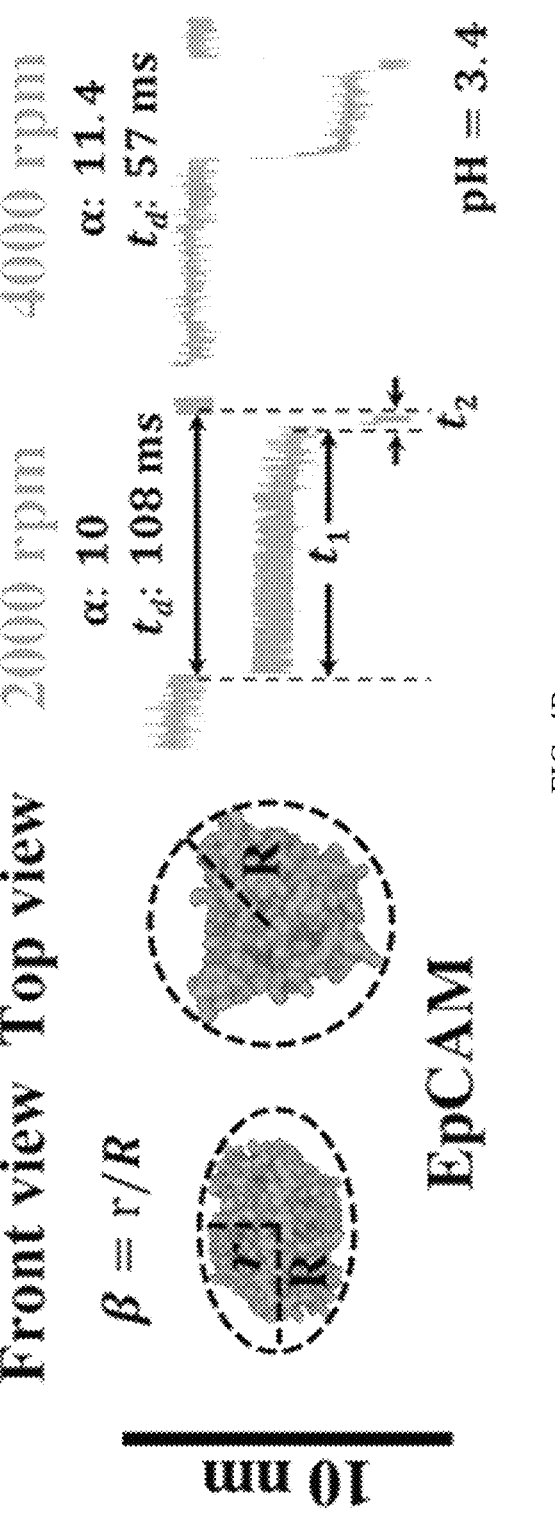
Figure 4C:
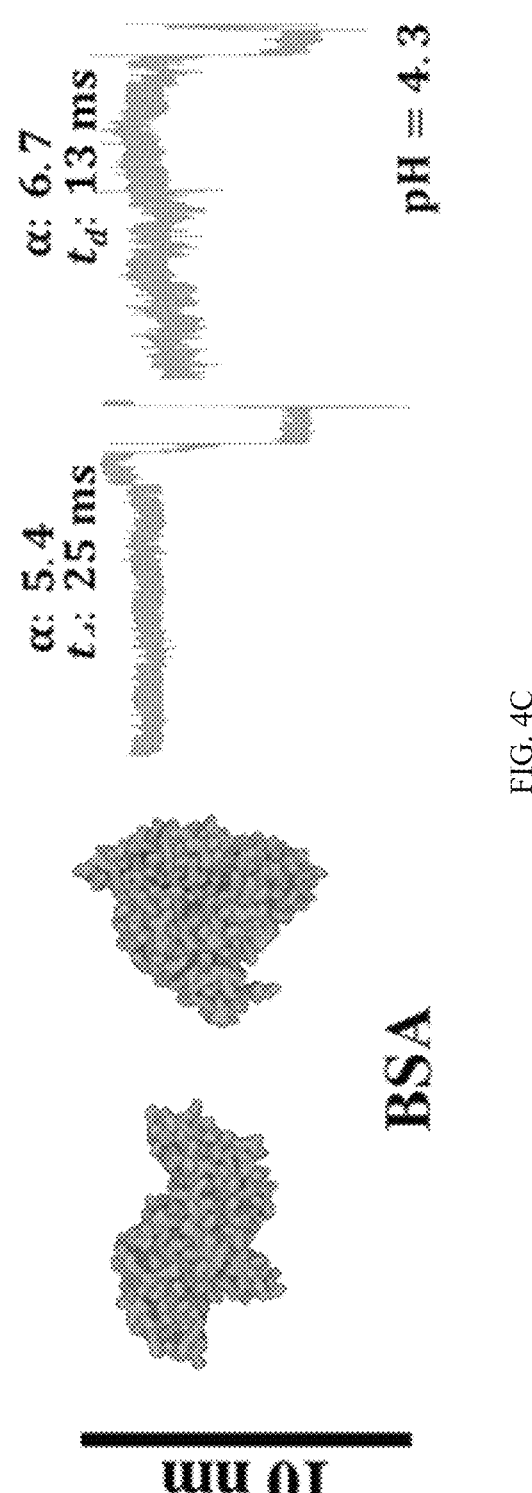
Figure 4D:
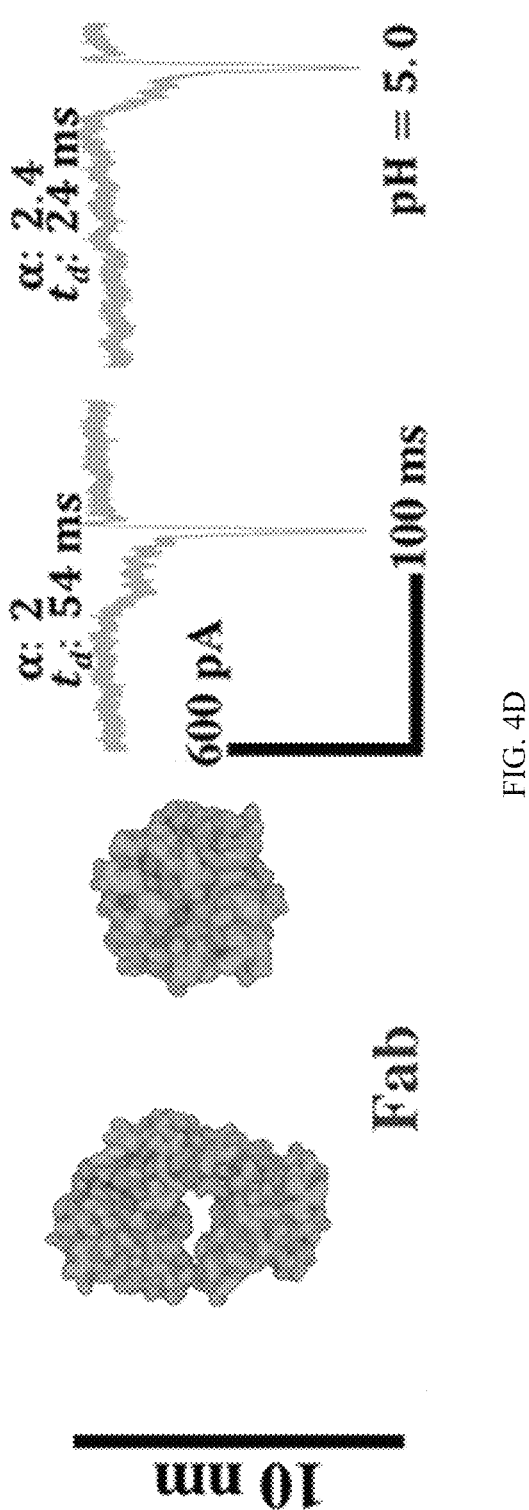
Figure 4E:
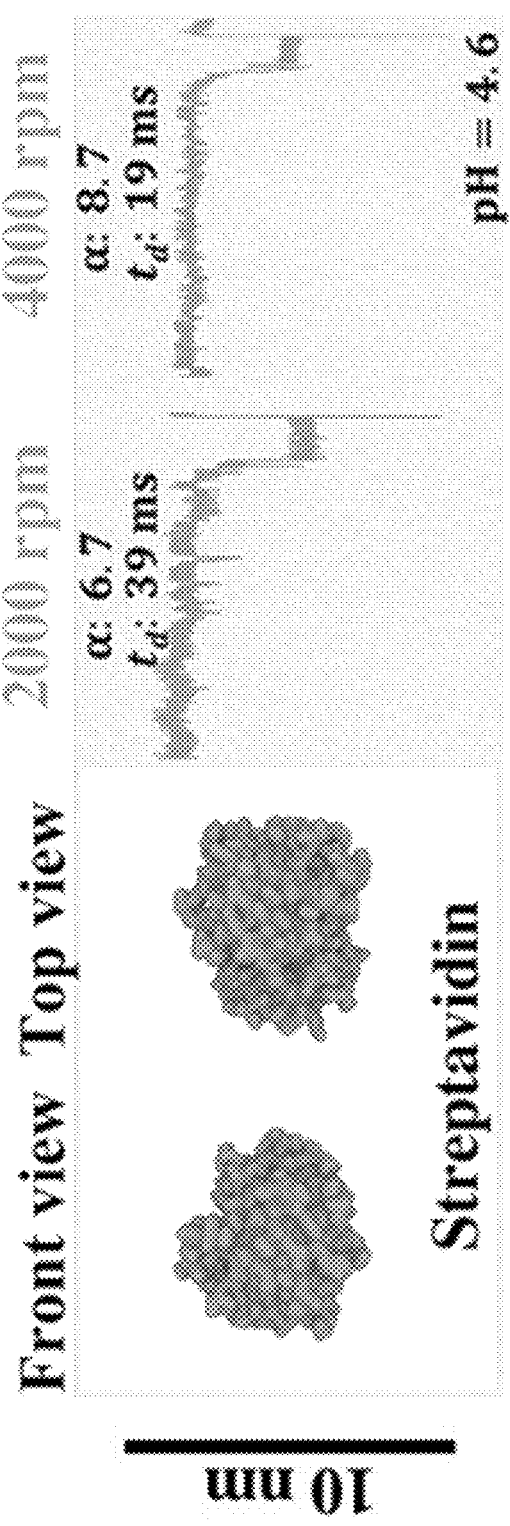
Figure 4F:
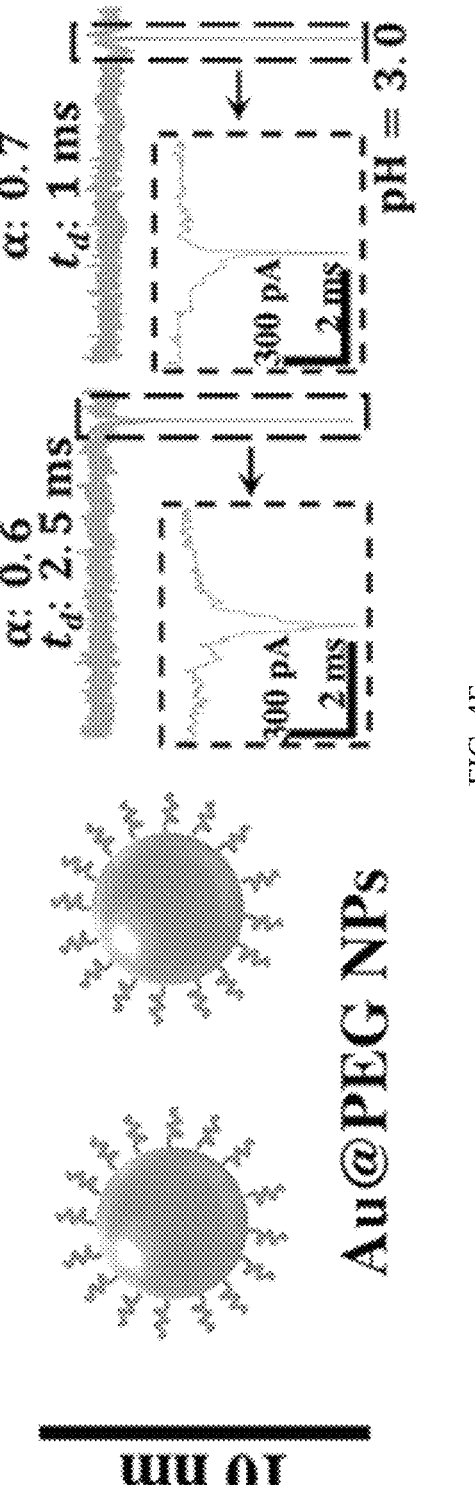
Figure 4G:
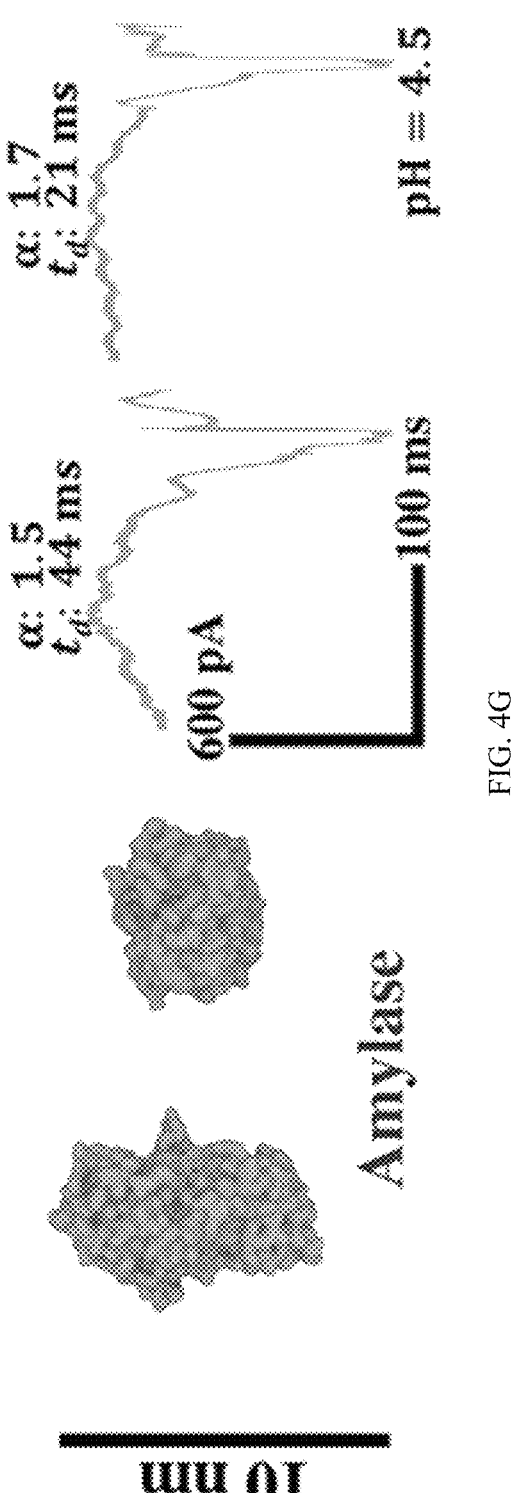
Figure 5A:
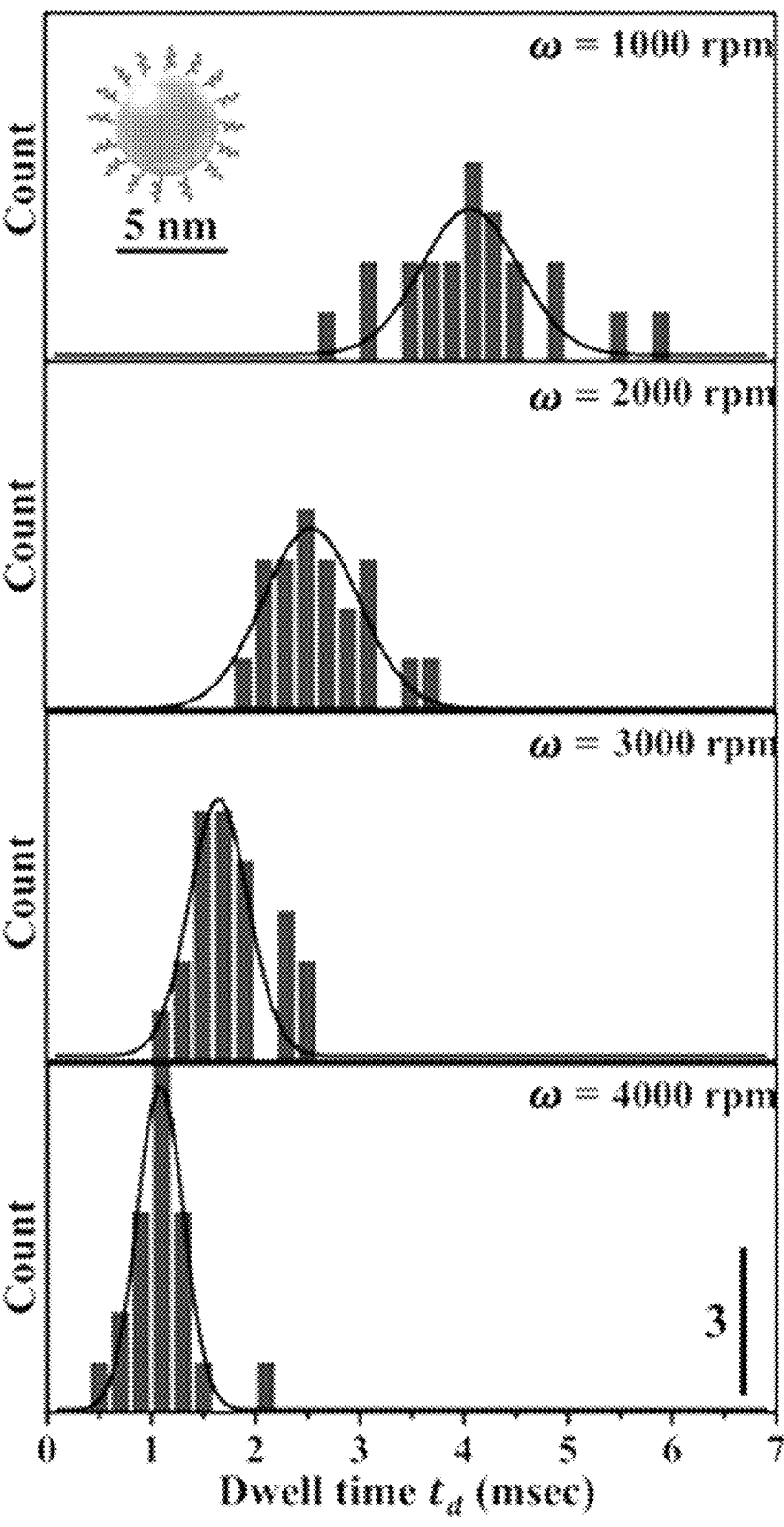
FIG. 5A shows a series of dwell time histograms of Au@PEG under different rotation speed detected by a device according to an embodiment of the subject invention.
Figure 5B:
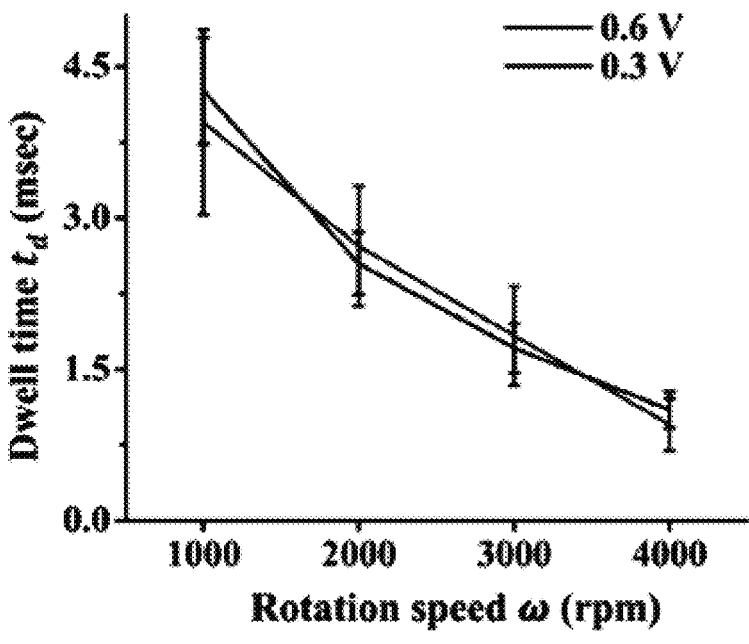
FIG. 5B is a graph showing dwell time versus rotation speed under different bias voltage for Au@PEG according to an embodiment of the subject invention.
Figure 5C:
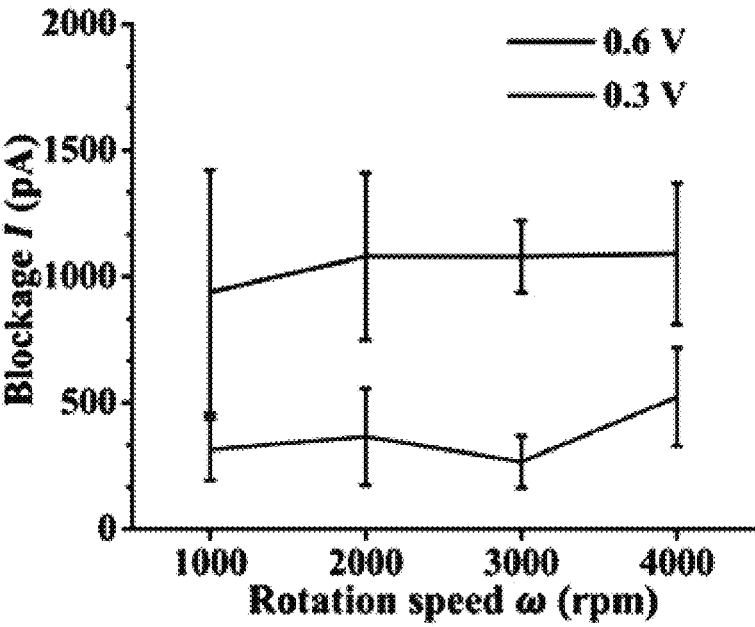
FIG. 5C is a graph showing the amplitudes of sensing signals of Au@PEG under different rotation speed and bias voltage values according to an embodiment of the subject invention.
Figure 5D:
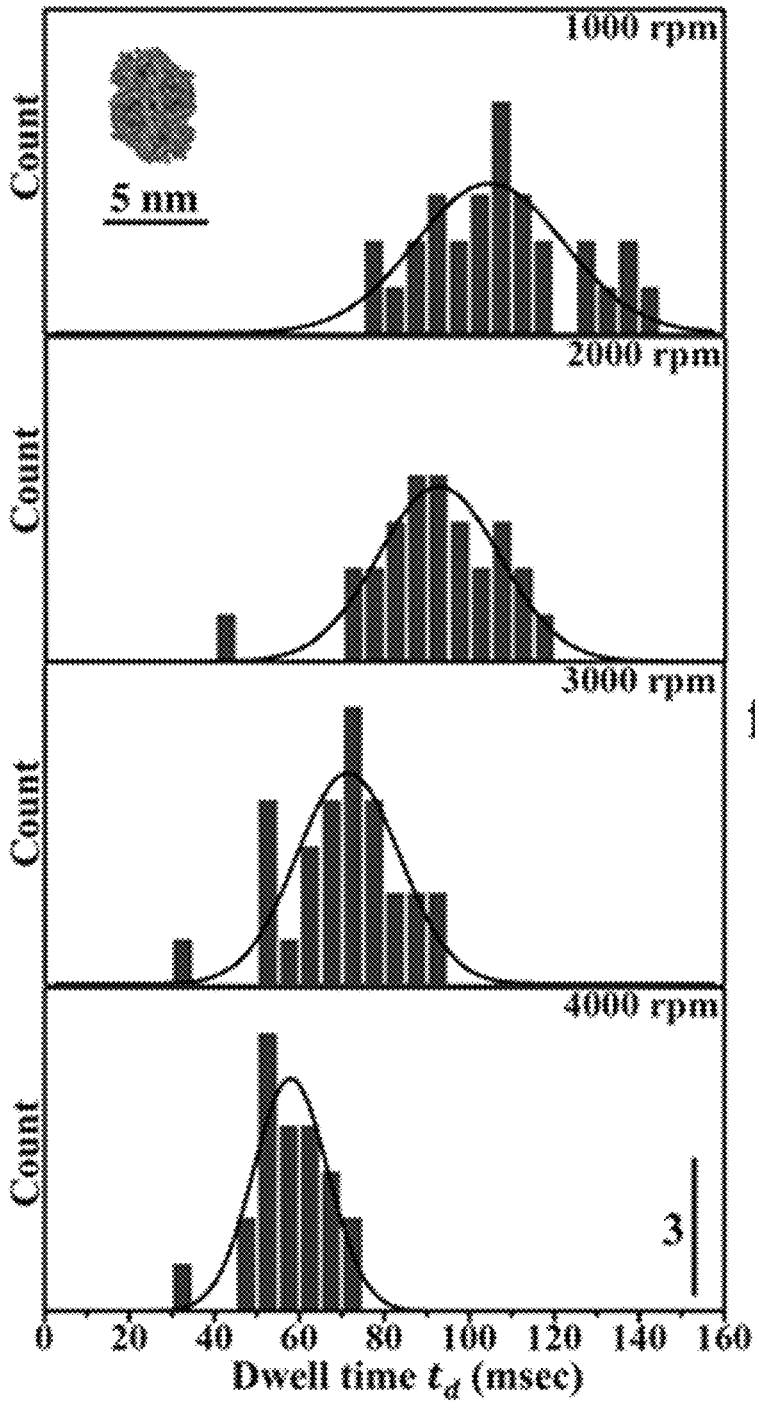
FIG. 5D shows a series of dwell time histograms of EpCAM under different rotation speed detected by a device according to an embodiment of the subject invention.
Figure 5E:
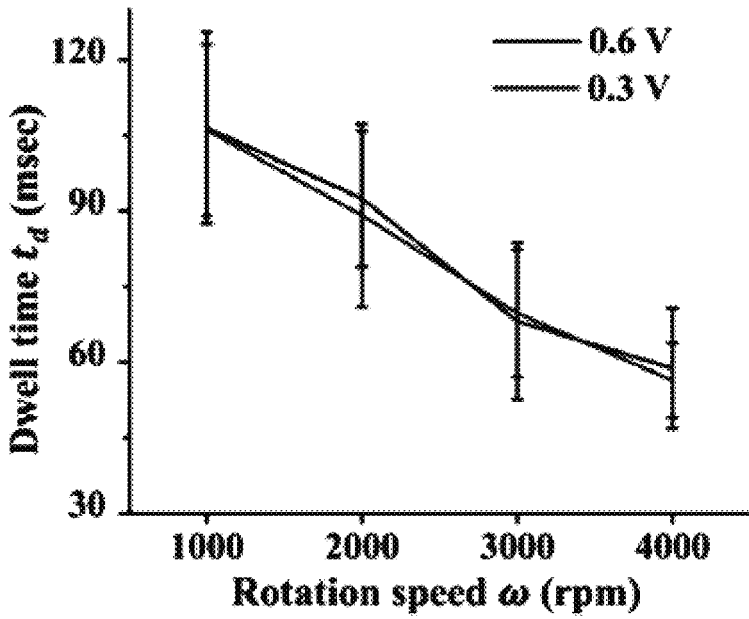
FIG. 5E is a graph showing dwell time versus rotation speed under different bias voltage for EpCAM according to an embodiment of the subject invention.
Figure 5F:
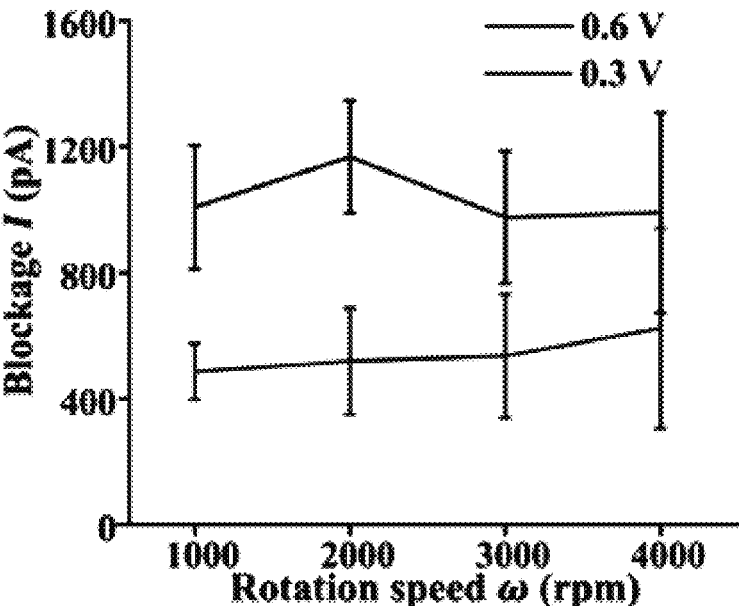
FIG. 5F is a graph showing the amplitudes of sensing signals of EpCAM under different rotation speed and bias voltage according to an embodiment of the subject invention.

This balanced state can be achieved by adjusting the pH value of the analyte medium or by adjusting the surface charge excited on the silicon nanopore using light (e.g., see FIGS. 2A and 2B). The inertial-kinetic molecular translocation provides a series of precise regulation on molecular translocation parameters, enabling the device to feedback molecular conformation with long dwell time and high signal-to-noise ratio single readout (e.g., see FIG. 3A to 3E). The single molecular fingerprinting capability of the provided nanopore device and/or method in sensing the mass, shapes, and configurations of different molecules and nanoparticles, including, for example, but not limited to, bovine serum albumin (BSA), Gold nanoparticles coated with polyethylene glycol (Au@PEG), epithelial cell adhesion molecules (EpCAM), EpCAM-antibody complex, Streptavidin, and α-Amylase, through quantifying the dwell time and detecting the characteristic sensing signals.

Embodiments of the subject invention and various advantages thereof will now be described with reference to exemplary embodiments in conjunction with the drawings.

Figure 1B:
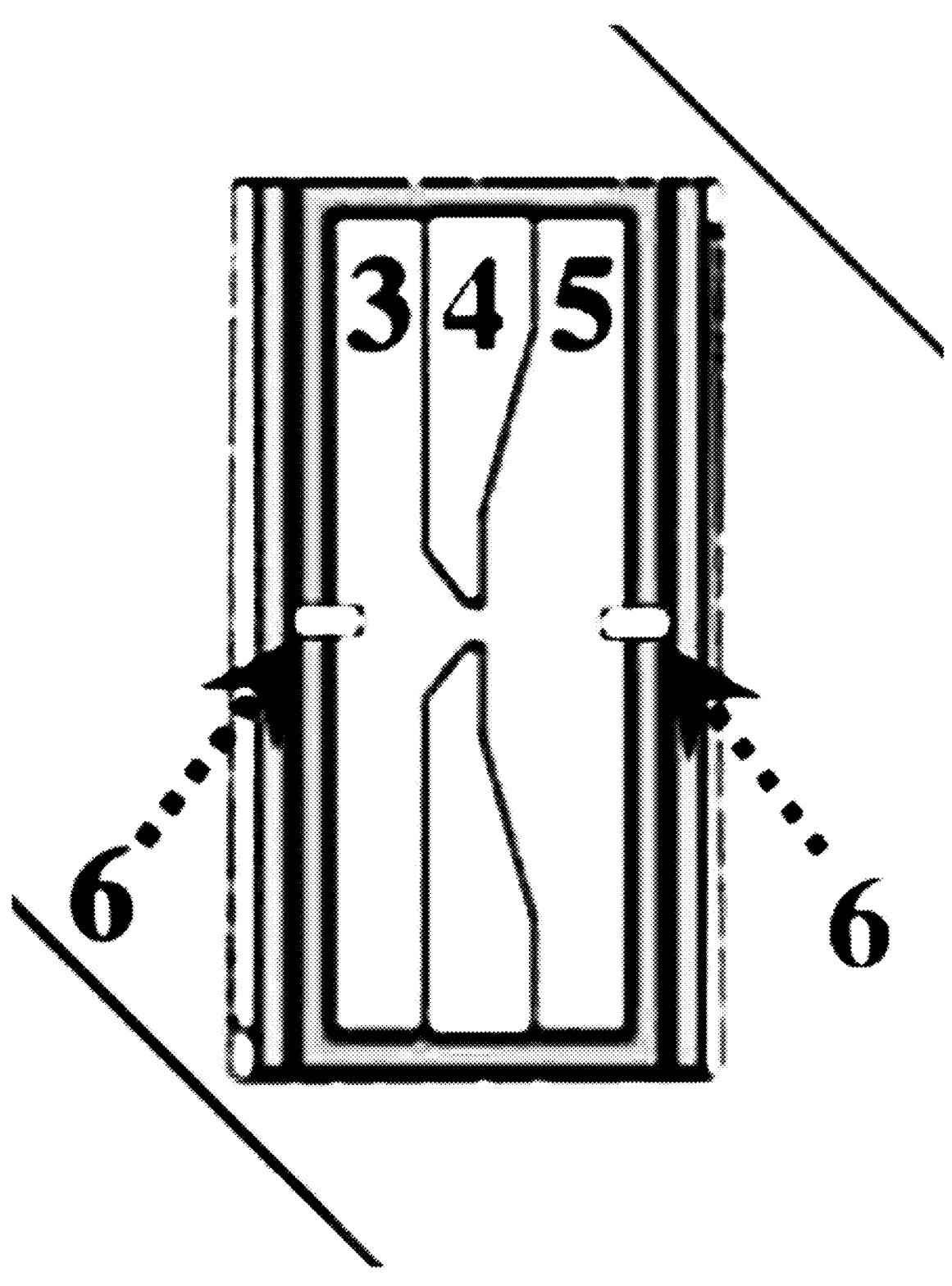
FIG. 1B is a detailed schematic of one detection module for one nanopore in one flow cell module according to an embodiment of the subject invention.
Figure 1C:
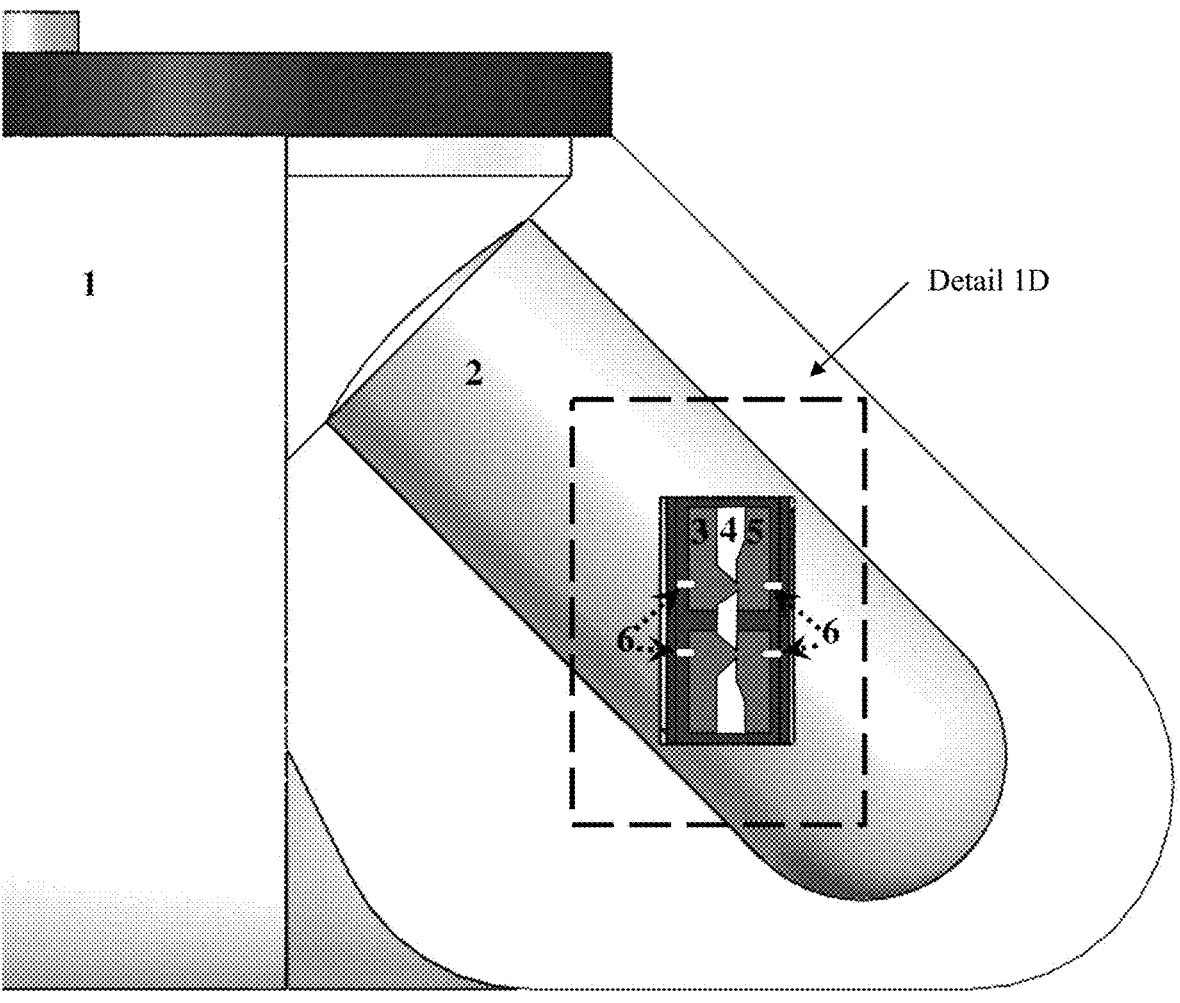
FIG. 1C is a schematic of an in-tube nanopore sensing device in a centrifuge with a nanopore module consisting of multiple nanopores in multiple flow cell modules wherein each nanopore has one signal detection module applying bias voltage and measuring signals according to an embodiment of the subject invention.
Figure 1D:
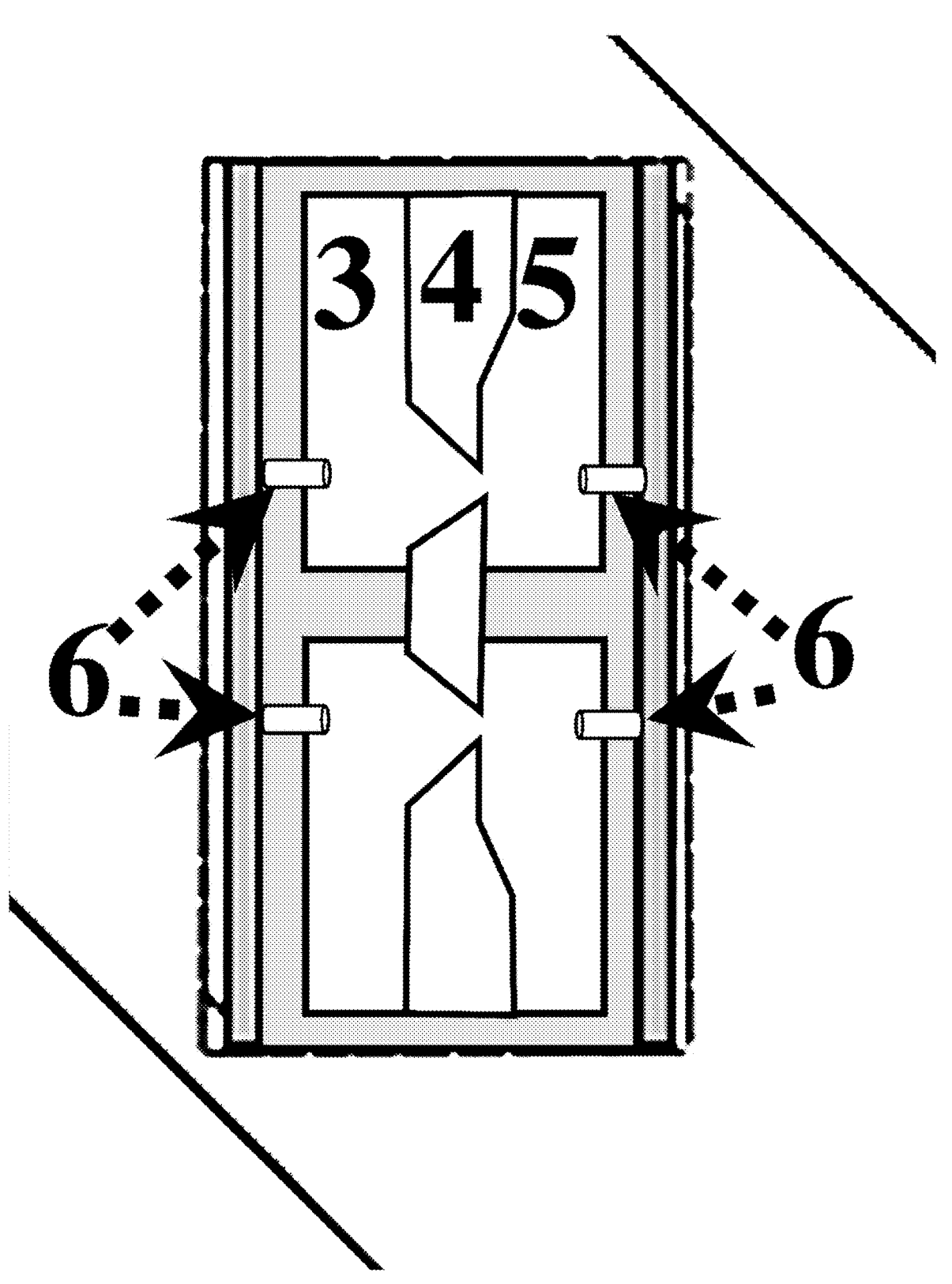
FIG. 1D is a detailed schematic of multiple detection modules for multiple nanopores in multiple flow cell modules according to an embodiment of the subject invention.
Figure 1E:
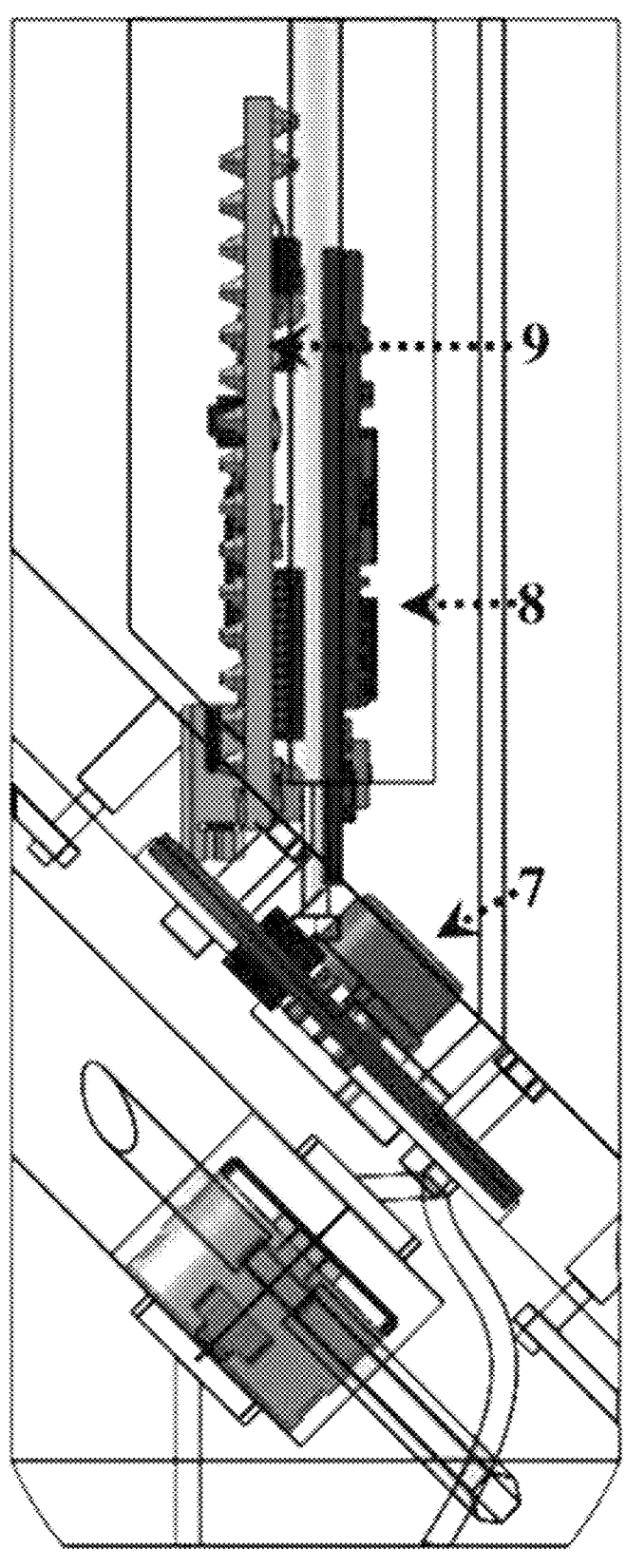
FIG. 1E is a schematic of a signal amplifier module, a control module, and a wireless communication module according to an embodiment of the subject invention.

One embodiment of the subject invention shown in FIGS. 1A-1C provides a nanopore sensing device, comprising:
a centrifuge rotor 1;
a centrifuge tube 2;
single or multiple flow cell modules 3 and 5;
a nanopore module consisting of single or multiple nanopores 4;
a signal detection module 6;
a signal amplifier module 7;
a control module 8; and
a wireless communication module 9.

A nanopore sensing device according to one embodiment of the invention is shown in FIGS. 1A-1E. To achieve controllable translocation of molecules, a nanopore module 4 is integrated in the upper and lower flow cells 3 and 5 of the flow cell modules to provide inertial-kinetically regulated molecular translocation, i.e., inertial-kinetic translocation, in a laboratory grade centrifuge, comprising a rotor 1 and a tube 2. While the conventional electrokinetic translocation behaviour of molecules is governed by the electrophoretic and electroosmotic velocities in nanopores, the inertial-kinetic translocation of molecules is mainly regulated by the centrifugal force with superposed counterbalancing forces due to electrophoretic and electroosmotic affects in the nanopore module 4 after introducing a constant biasing potential between its two sides by signal detection modules 6.

Several in-tube modules, comprising signal amplifier module 7, Analog-to-Digital converter (ADC) and microcontroller of control module 8, and wireless communication module 9, are successively connected and fixed in tube to provide amplification, testing, and wireless transmission of sensing signal. In certain embodiments, the microcontrollers can integrate the ADC to avoid additional wiring noise and other sources of interference or signal degradation. The preamplifier circuit board 7 sets the sensitivity of the circuit, which corresponds to the signal amplitude of the protein and nanoparticles generated in the nanopore. A noise-free cascode and low-noise processing based on differential amplifier circuit makes the preamplifier circuit board 7 an excellent low-level signal detector. Sampling rate of control module 8 is set (e.g., set to 50 kHz) to maintain conformational sensitivity of sensing signals with long dwell time (>1 ms). Here, the conformational sensitivity means shape and statistical properties of signal pulses, which enables to analyze a biomolecular species in solution [ACS Nano, 8, 6, 6425-6430, 2014; Nature Nanotechnology, 16, 2021, 1244-1250].

When a nanopore module 4 is centrifuged, centrifugal force can effectively capture and translocate a single molecule through a nanopore by overcoming Brownian motion and potential barrier ($\Delta U$) due to the molecule-pore interaction. Overcoming $\Delta U$ means the biomolecule needs to overcome chemical pore-particle interactions to enter the pore [ACS Nano 2020, 14, 15816-15828]. The measured sensing signals clearly delineate three distinct stages related to the inertial-kinetic translocation in the nanopore module 4, including (i) molecule outside the sensing zone, (ii) molecule inside the sensing zone, and (iii) molecule passing through the nanopores, as show in FIGS. 2C-2D. The molecular motions in stages (i) and (ii) are governed by centrifugal force and Brownian motion, while centrifugal force and potential barrier become dominant on the molecular behaviour in stage (iii).

MATERIALS AND METHODS

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Validation of Inertial-Kinetics-Translocation Mechanisms

To confirm the fingerprinting-resolution detecting function of a nanopore sensing device according to an embodiment of the subject invention, an in-tube device comprising a 15-nm nanopore was used to sense six representative molecules, each respectively having a unique mass and shape, comprising EpCAM, BSA, fragment antigen-binding (Fab), streptavidin, Au@PEG, and α-Amylase. For each molecule a low molecular concentration of −0.1 nM was used to minimize molecular interaction and was injected simultaneously into the flow cell 3 of the in-tube device. Each molecular motion is reflected in the recorded current blockage signal, including the current baseline related to stage (i), the first current drop and duration ($t_1$) associated with molecular capture in stage (ii), and the second current drop and duration ($t_2$) due to molecular translocation in stage (iii). The dwell time $t_d$ is calculated as $t_1+t_2$. Molecular translocation sensing was then performed at different rotation speeds. The capture current blockage signal pulses indicate that the dwell time and the time ratio are related to the molecular weight m, the molecular shape K', and the rotation speed a, demonstrating the distinguishable translocation characteristics of individual molecules, as shown in FIGS. 4A-4G.

Au@PEG and EpCAM were tested with the device under different bias voltages and rotation speeds, as shown in FIGS. 5A-5F. For instance, a 100 kDa biomolecule experiences centrifugal force of $2.3\times10^{-6}$ pN at 2000 rpm and $9.2\times10^{-6}$ pN at 4000 rpm. The histograms of Au@PEG's dwell time (FIG. 5A) indicate that both the mean and standard deviation thereof decreases with the increase of the rotation speed ω, while being independent on the level of bias voltage (FIG. 5B) in the inertial-kinetically regulated molecular translocation events. The amplitude of signals (FIG. 5C) was found to be independent of the rotation speed and increasing with the bias voltage. As for EpCAM (FIGS. 5D-5F), similar characteristics of molecular translocation in terms of the rotation speed ω, and versus bias voltages were shown. Dwell times of Au@PEG and EpCAM were different by more than one order of magnitude due to their different molecular weight (or mass), although they have similar sizes of around 5 nm. For sensing of molecules, the dwell time and amplitude of signal pulses can be advantageously optimized by adjusting the rotational speed and bias voltage.

Figure 6A:
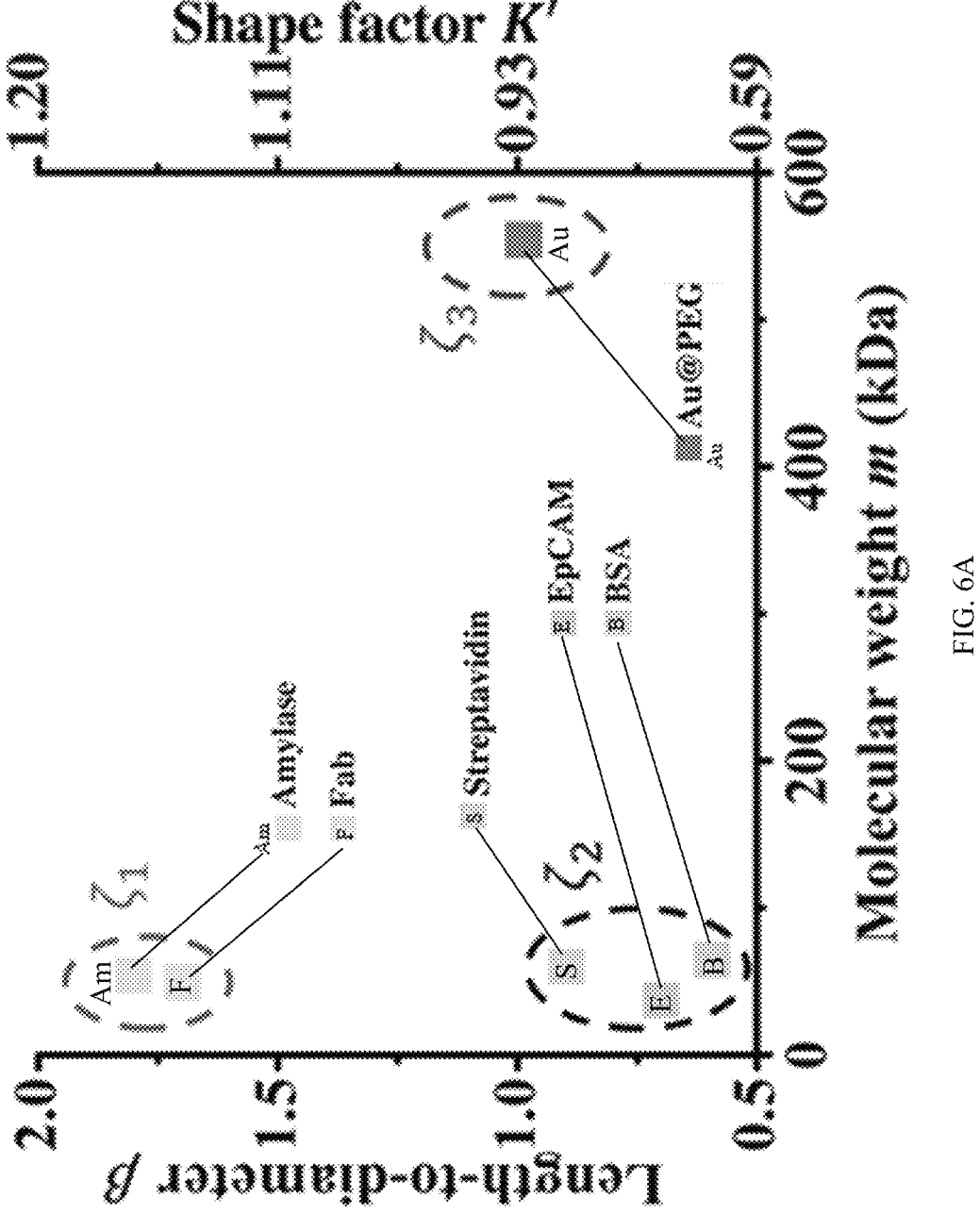
FIG. 6A shows a mass and shape distribution of molecules according to an embodiment of the subject invention. Six molecules can be divided into three categories according to their shape-to-mass weighting factors zeta (ζ), i.e., K'/m, including $\zeta_1$ (Amylase, Fab), $\zeta_2$ (Streptavidin, EpCAM, and BSA), and $\zeta_3$ (Au@PEG), and $\zeta_1>\zeta_2>\zeta_3$. Here K' is the shape factor determined solely by molecular length-to-diameter ratio of molecule β and m is molecular weight.
Figure 6B:
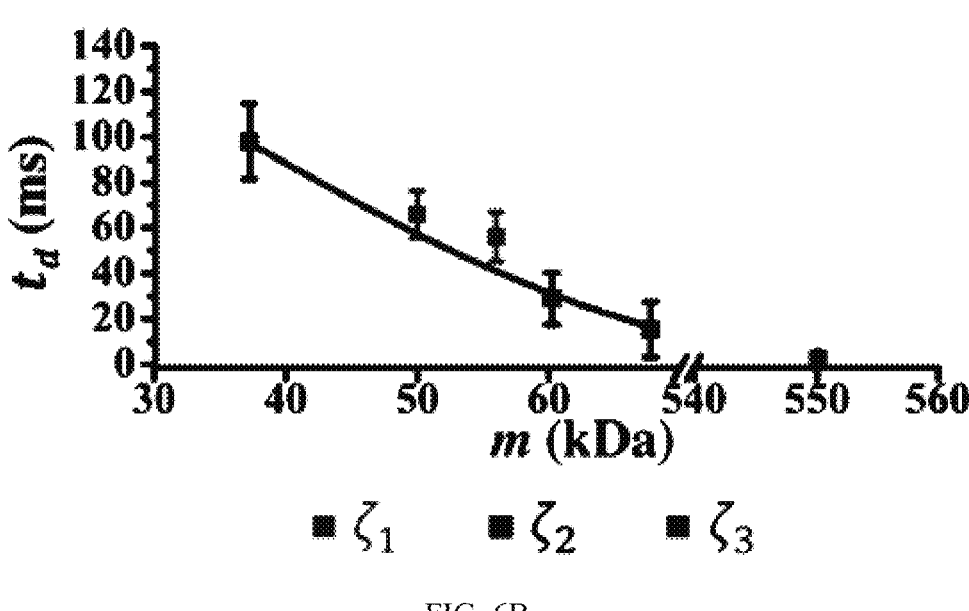
FIG. 6B is a graph showing dwell time measured at rotation speed of 2000 rpm according to an embodiment of the subject invention.
Figure 6C:
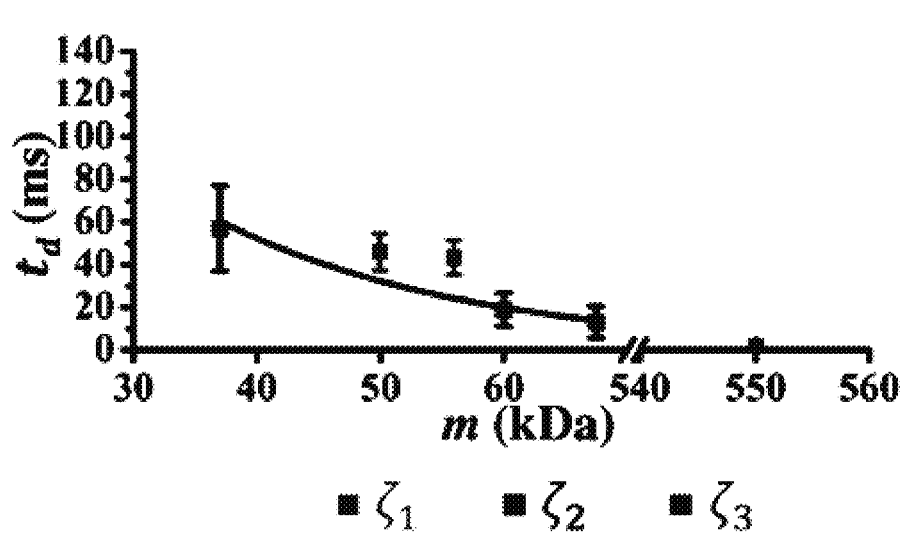
FIG. 6C is a graph showing dwell time measured at rotation speed of 4000 rpm according to an embodiment of the subject invention.
Figure 6D:
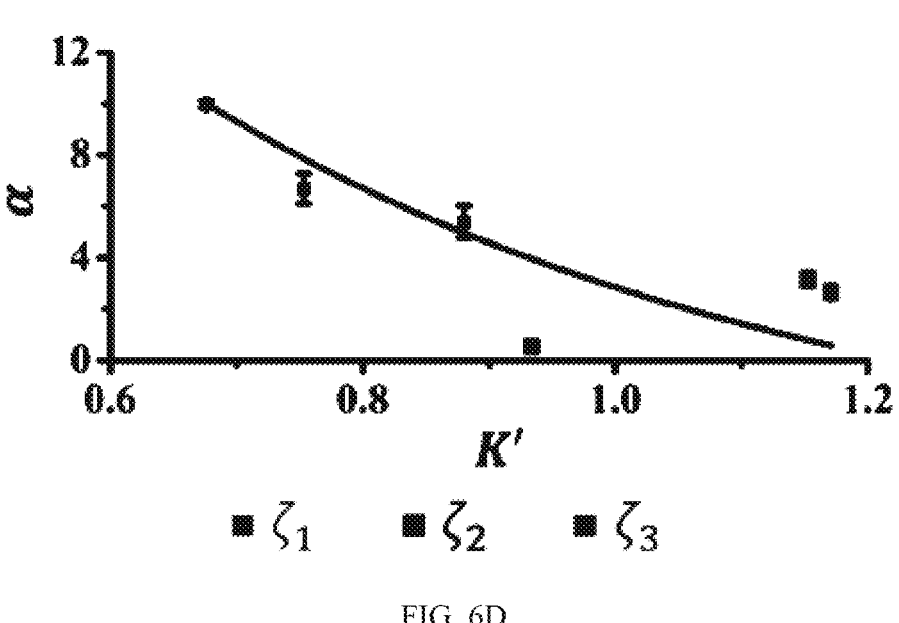
FIG. 6D is a graph showing time ratio measured at rotation speed of 2000 rpm according to an embodiment of the subject invention.
Figure 6E:
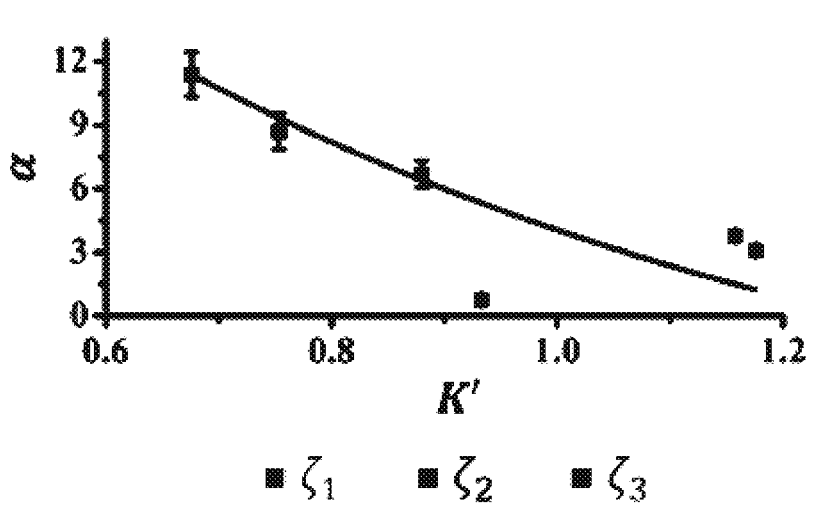
FIG. 6E is a graph showing time ratio measured at rotation speed of 4000 rpm according to an embodiment of the subject invention.

To verify the capability of this nanopore sensing device according to an embodiment of the subject invention for characterizing the mass and shape of molecules, the tested molecules were first divided into three categories according to their shape-to-mass weighting factors ζ, as shown in FIG. 6A. The detected data of the nanopore sensing device (FIGS. 6B-6C) exhibits an exponential decay of dwell time with the molecular mass, while a faster decay on dwell time is observed at a higher centrifugal rotation speed. Meanwhile, the results of category $\zeta_1$ molecules suggest a slower decay rate than that of category $\zeta_2$ due to their bigger shape-to-mass weighting factors, as shown in FIGS. 6B-6C. As for the correlation between α and K', the time ratio exponentially decays with the shape factor, and the results of category $\zeta_1$ molecules demonstrate a slower decay rate than that of category $\zeta_2$, as shown in FIGS. 6D-6E.

During the molecular capturing process, molecular motions are governed by the competition between centrifugal force and Brownian diffusion and can thus be described using the Langevin equation.

$$v(\beta) = \frac{1}{kT}D(\beta)f_e(\beta) + \sqrt{2D(\beta)}\,g(t) \tag{1}$$

where, $v_{(\beta)}$ is velocity of the molecules, $f_e(\beta)=f_c$, and g(t) is the Gaussian noise term resulting from random collision forces.

Additionally, based on the Einstein-Smoluchowski Relation, the diffusion coefficient D(β) of a molecule can be described as:

$$D(\beta) = \frac{kT}{f(\beta)} \tag{2}$$

where, k is the Boltzmann constant, T is the environmental temperature, and f(β) is viscous drag coefficient; the molecular diffusion coefficient is highly related to molecular shape K'. Therefore, the capture duration $t_1$ can be calculated using the equation $12\pi\mu RK'L/f_c$, where $\mu$ represents dynamic viscosity coefficient of molecules, R represents equatorial semi-axis of molecules, L represents sensing length and $f_c$ represents centrifugal force exerted on molecules. As for molecular motions during translocation-through-nanopore process (e.g., see FIG. 2Diii), translocation time $t_2$ (time until desorption) is a stochastic variable dependent on bulk dissociation rate.

Thus, $t_2$ can be calculated using an Eyring-like form $$t_0 e^{-\frac{h(f_c - f_{drag1})}{kT}},$$

where h represents the force-dependent factor, $t_0$ represents the mean of the exponential distribution, $f_{drag1}$ represents viscous force opposite to molecular motion induced by $f_c$, k represents Boltzmann constant and T represents environmental temperature. Consequently, the time ratio $\alpha$ and dwell time $t_d$ can be calculated using the following equations:

$$\alpha = \frac{12\pi\mu RK'L}{f_c t_0 e^{-h(f_c - f_{drag1})/kT}} = \frac{12\pi\mu R\zeta L}{\rho\omega^2\left(t_0 e^{-\frac{h}{kT}(m\rho\omega^2 - 6\pi\mu RK')}\right)} \quad (3)$$

$$t_d = \frac{12\pi\mu RK'L}{fc} + t_0 e^{-\frac{h(f_c - f_{drag1})}{kT}} = \frac{12\pi\mu R\zeta L}{\rho\omega^2} + t_0 e^{-\frac{h(m\rho\omega^2 - 6\pi\mu R\zeta m)}{kT}} \quad (4)$$

Here m is the molecular weight, $\zeta$ is the shape-to-mass weighting factors, $\rho$ is distance between the targets and the rotating shaft of the centrifuge, and $\omega$ is the rotation speed.

Example 2—Longitudinal Monitoring Results on Sensing the Complex

Figure 7A:
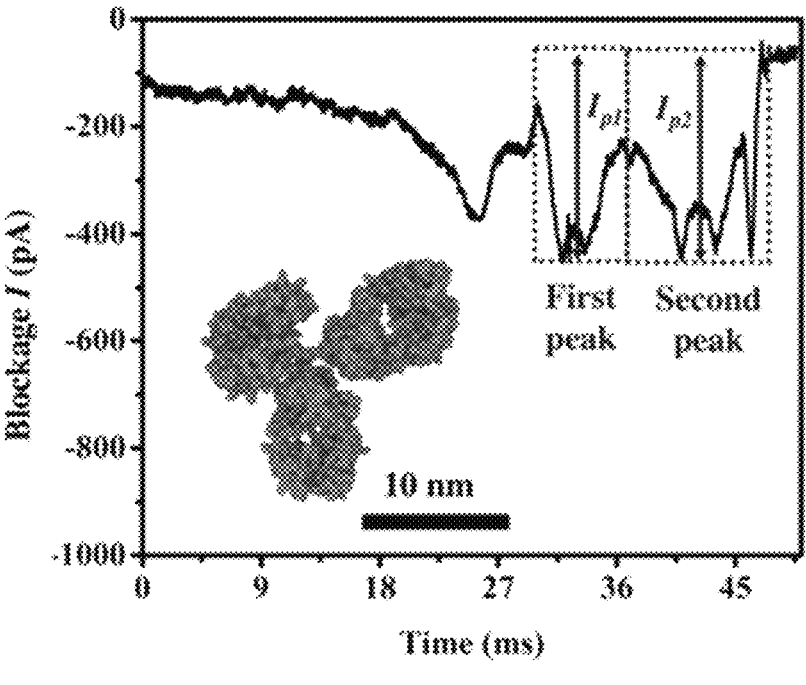
FIG. 7A is a graph showing sensing signals of antibody EpCAM IgG according to an embodiment of the subject invention.
Figure 7B:
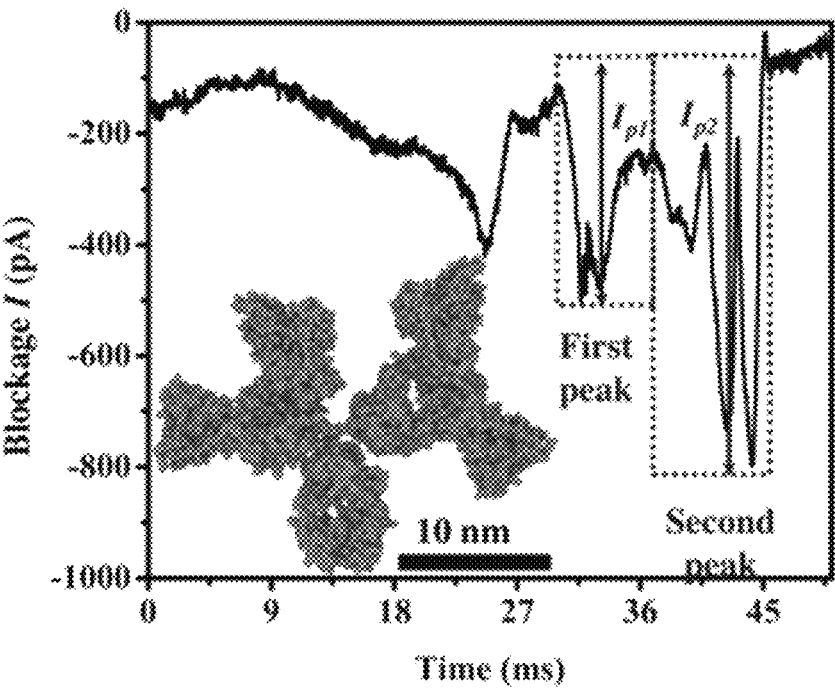
FIG. 7B is a graph showing sensing signals of antibody-antigen complex EpCAM IgG-EpCAM according to an embodiment of the subject invention.
Figure 7C:
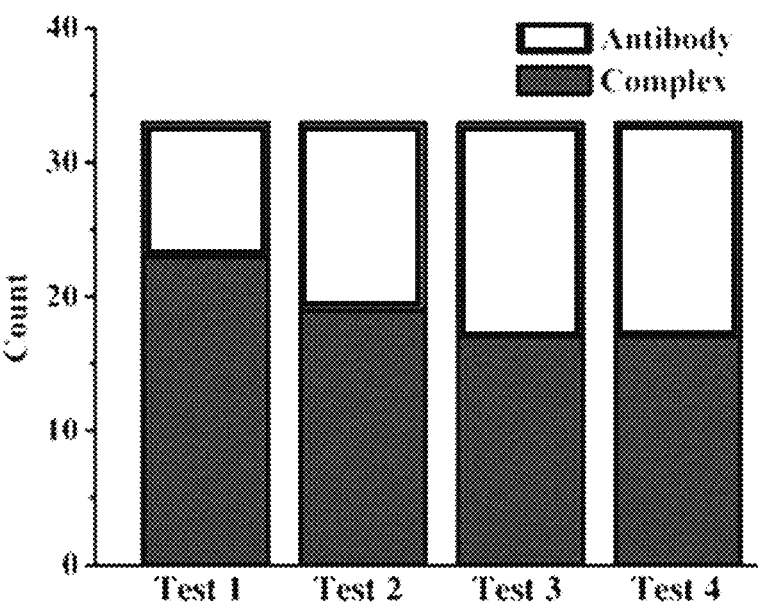
FIG. 7C shows longitudinal monitoring of dissociation of antibody-antigen complex according to an embodiment of the subject invention.

To validate the longitudinal monitoring function of a nanopore sensing device according to an embodiment of the subject invention, the device was used for detecting the morphological changes caused by molecular interactions, such as the dissociation of EpCAM IgG (antibody) and EpCAM (antigen) complex. Comparing the characteristic signal traces of antibody molecule and antibody-antigen complex, it was found that the signal of the complex has a larger ratio of second-peak amplitude to first-peak amplitude ($I_{p2}/I_{p1} \geq 1.5$) than that of the antibody ($I_{p2}/I_{p1} \leq 1.0$), as shown in FIGS. 7A-7B. The signatures in signal traces provides a novel and advantageous approach to evaluate the binding affinity of the antibody-antigen complex. The dissociation sensing experiment was repeated after every 20 minutes and performed 4 times in total, which signified that the EpCAM IgG-EpCAM complex gradually dissociated along with the time at the balanced state and the ratio of the complex to antibody in solution was observed to decrease gradually with the time, as shown in FIG. 7C.

Figure 7D:
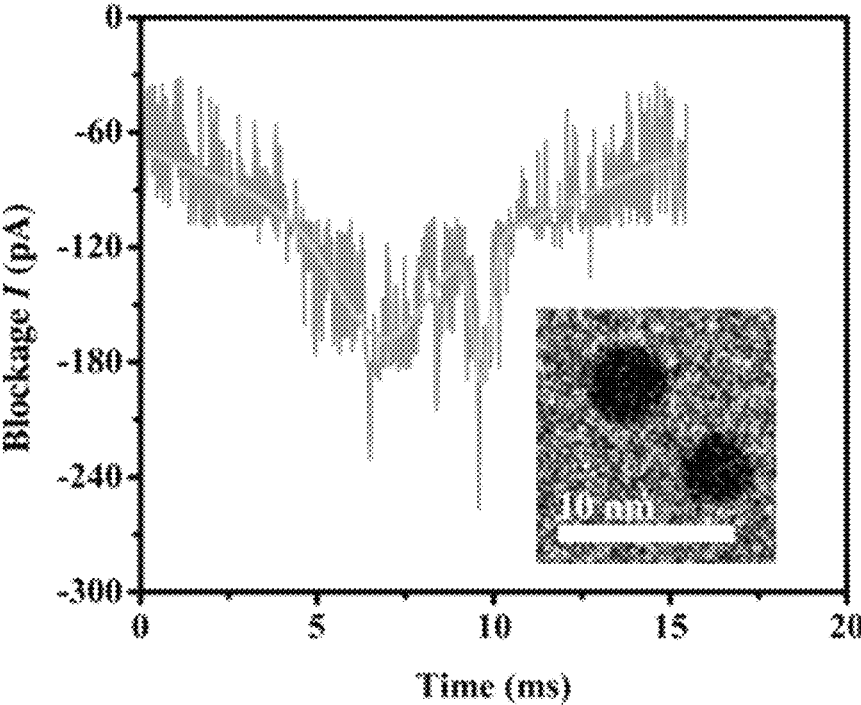
FIG. 7D is a graph showing sensing signal traces of Au@PEG nanoparticles in bimolecular aggregation according to an embodiment of the subject invention.
Figure 7E:
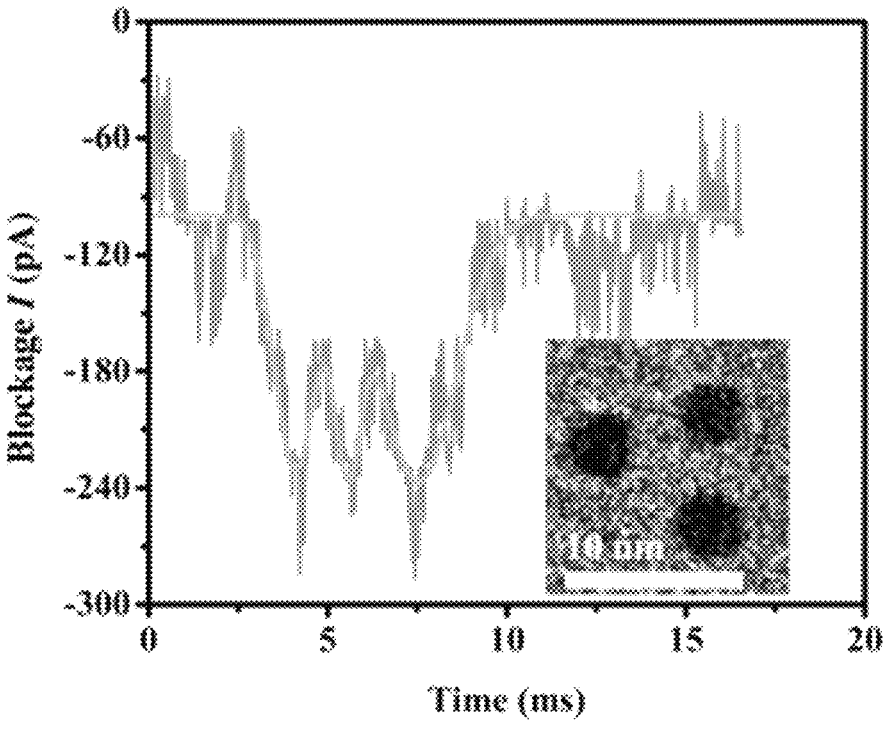
FIG. 7E is a graph showing sensing signal traces of Au@PEG nanoparticles in trimolecular aggregation according to an embodiment of the subject invention.
Figure 7F:
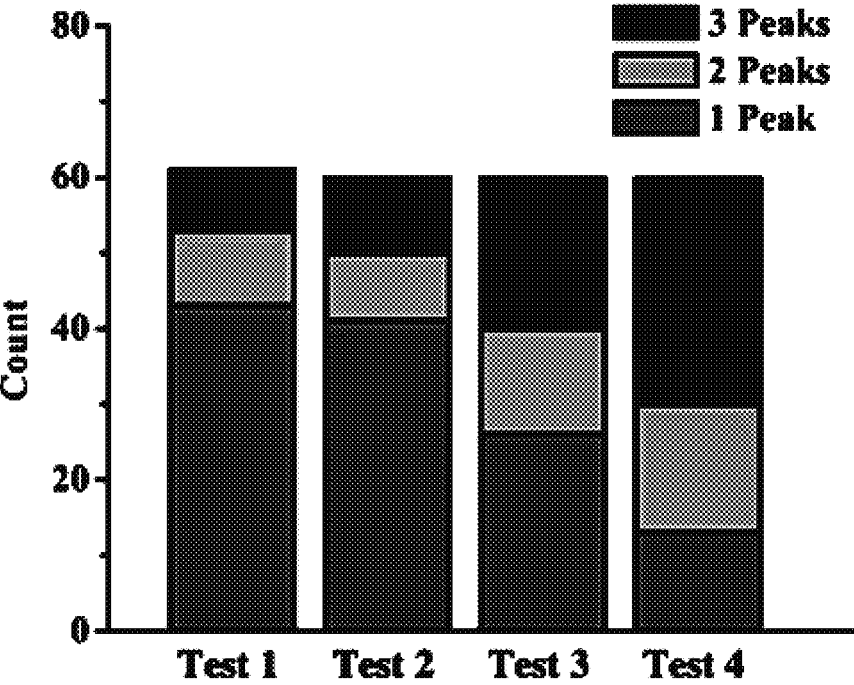
FIG. 7F shows longitudinal sensing of aggregation of Au@PEG nanoparticles according to an embodiment of the subject invention.

Embodiments of the provided nanopore sensing device can also be used to longitudinally detect the morphological changes of molecules during molecular aggregation and polymerization. To demonstrate this, the initial Au@PEG solution was first treated with ultrasound, then the aggregation sensing experiment was repeated after every 10 minutes and totally performed 4 times. The characteristic sensing signals of Au@PEG in single nanoparticle, bimolecular aggregation, and trimolecular aggregation exhibit single-peak, two-peaks, and three-peaks, respectively, as shown in FIGS. 7D-7E. Using these features (e.g., counting the number of peaks per molecule translocation) of signal readouts, the proportion of bimolecular and trimolecular aggregations in the Au@PEG nanoparticles solution were found gradually increasing and eventually exceeding that of single nanoparticle along with the time, as shown in FIG. 7F. Here, the 4.8-nm spherical nanoparticles Au@PEG were synthesized using a kinetically controlled seeded growth method. Initially, 3.5-nm Au seeds were synthesized by injecting tetrachloroauric acid into a mixed solution of sodium citrate and tannic acid at 70° C. Subsequently, the size of the Au seeds was increased to 4.8 nm by diluting the seed solution and injecting aliquots of gold precursor [Chem. Mater. 28, 1066-1075 (2016)].

Example 3—Programmable Translocation Direction

Figure 8A:
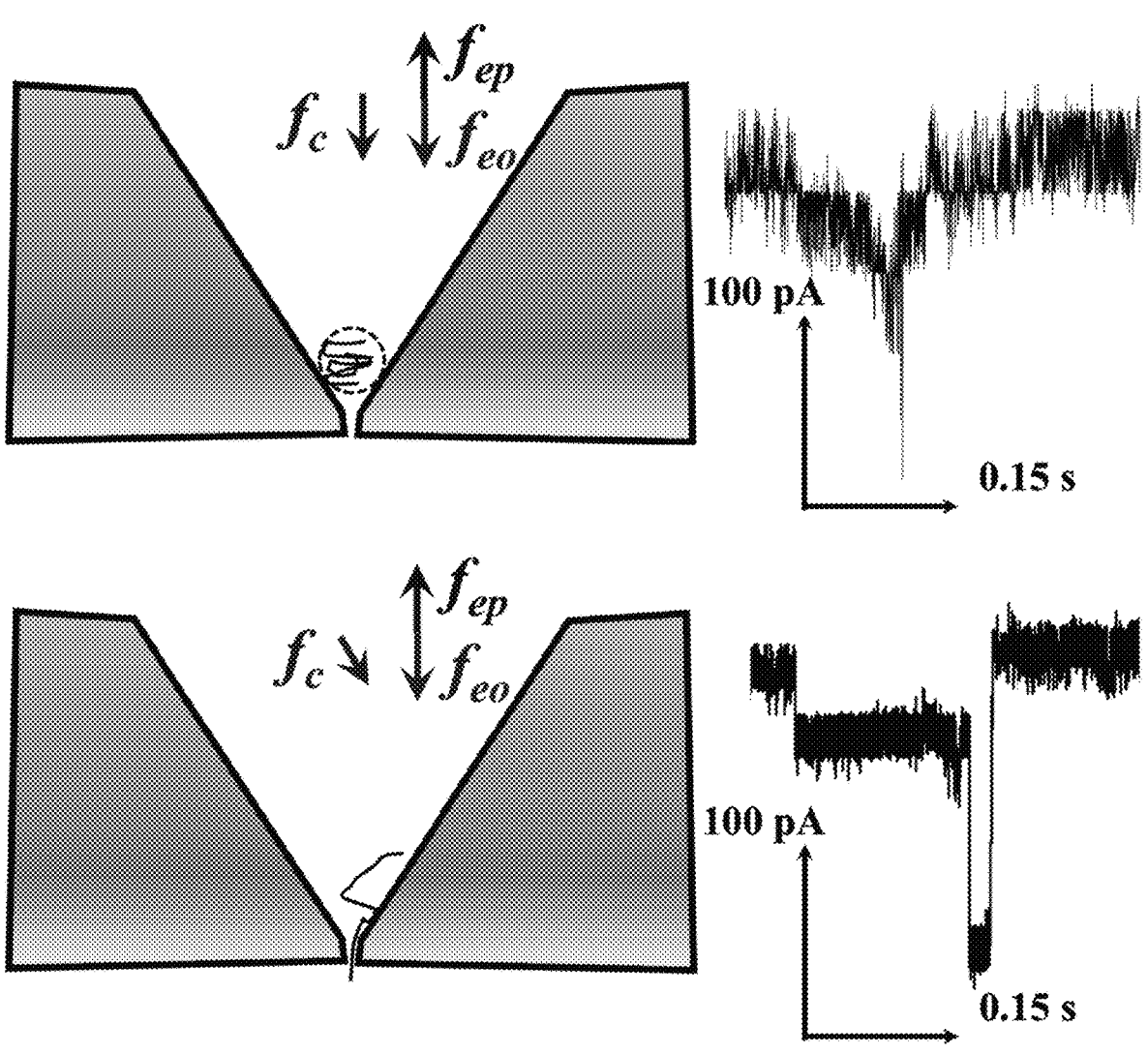
FIGS. 8A-8C show sensing signals of the molecules (i.e., $PEG_{10000}$ chains) under different direction of exerted centrifugal forces. When centrifugal force is normal to the nanopore (FIG. 8B), and the centrifugal force is normal to the etched sidewall (FIG. 8C).
Figure 8B:
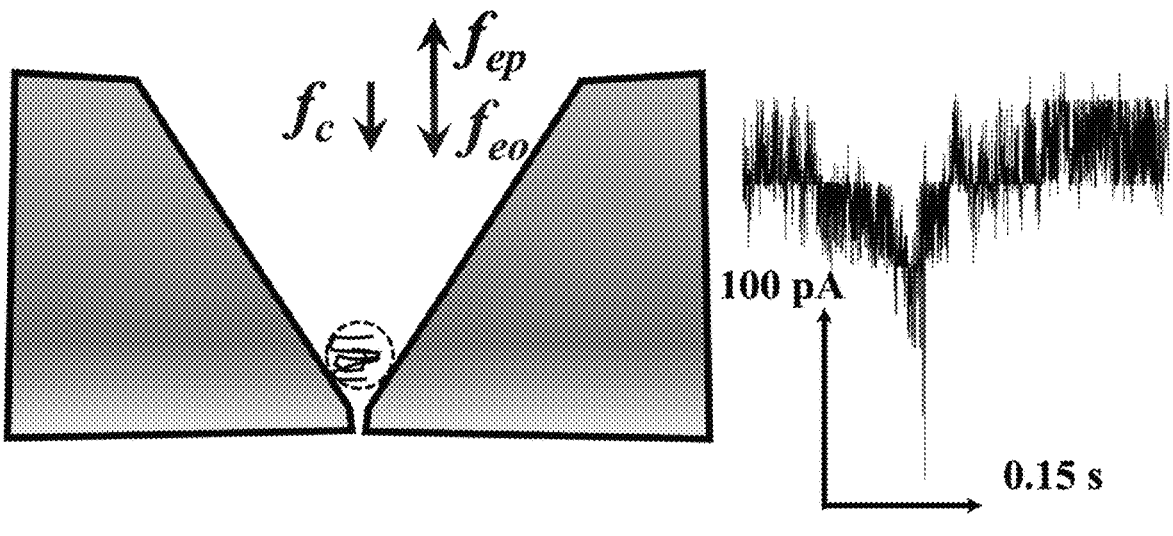
Figure 8C:
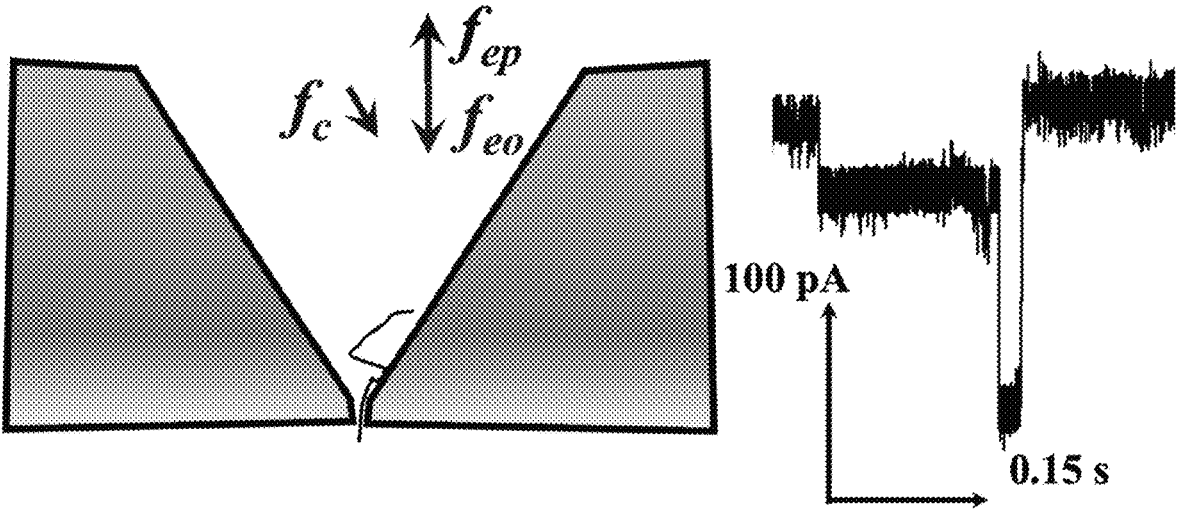
Figure 9A:
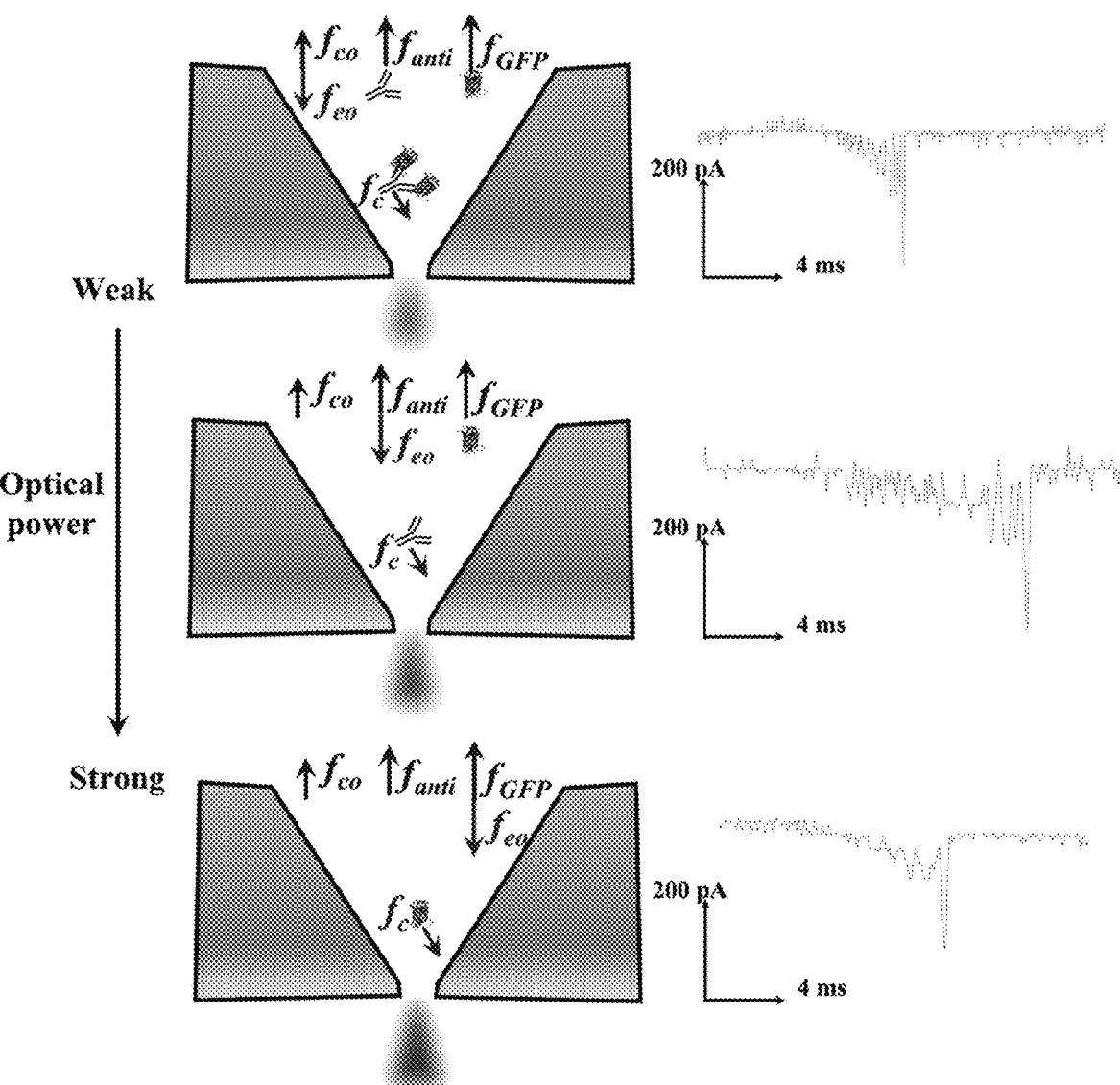
FIGS. 9A-9D show selective sensing signals of green fluorescence proteins (GFP)-antibody conjugates (FIG. 9B), antibody (FIG. 9C), and GFP (FIG. 9D) measured in illumination with specific power of 60 mW, 75 mW, and 110 mW, respectively.
Figure 9B:
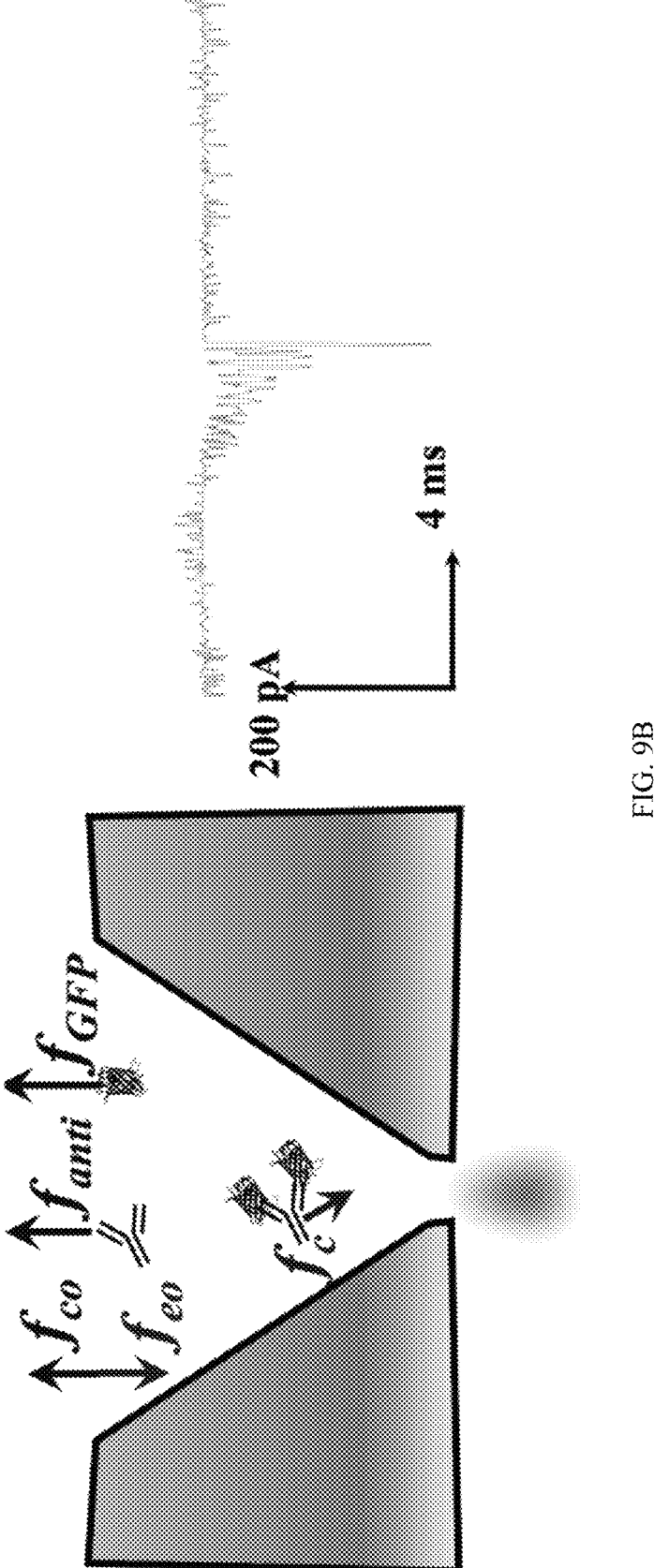
Figure 9C:
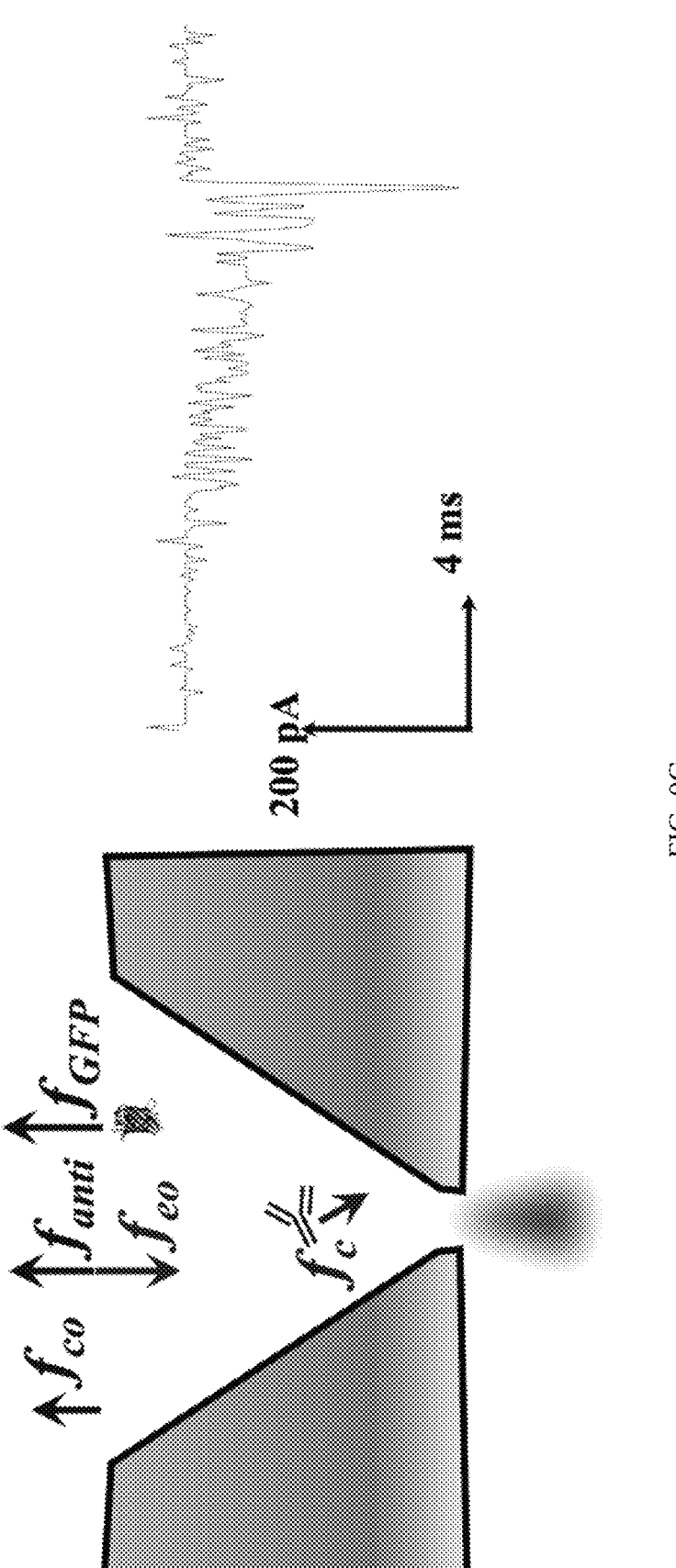
Figure 9D:
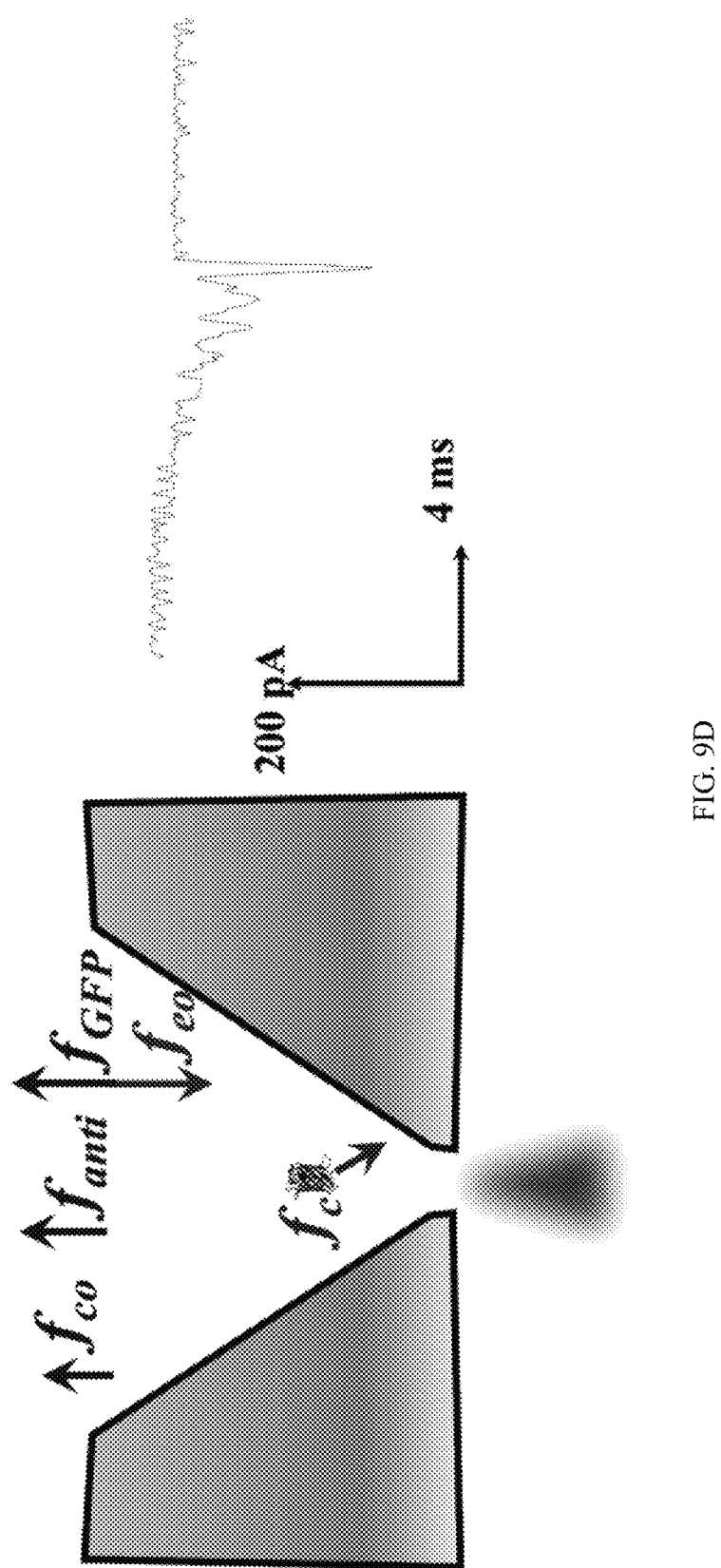
Figure 10:
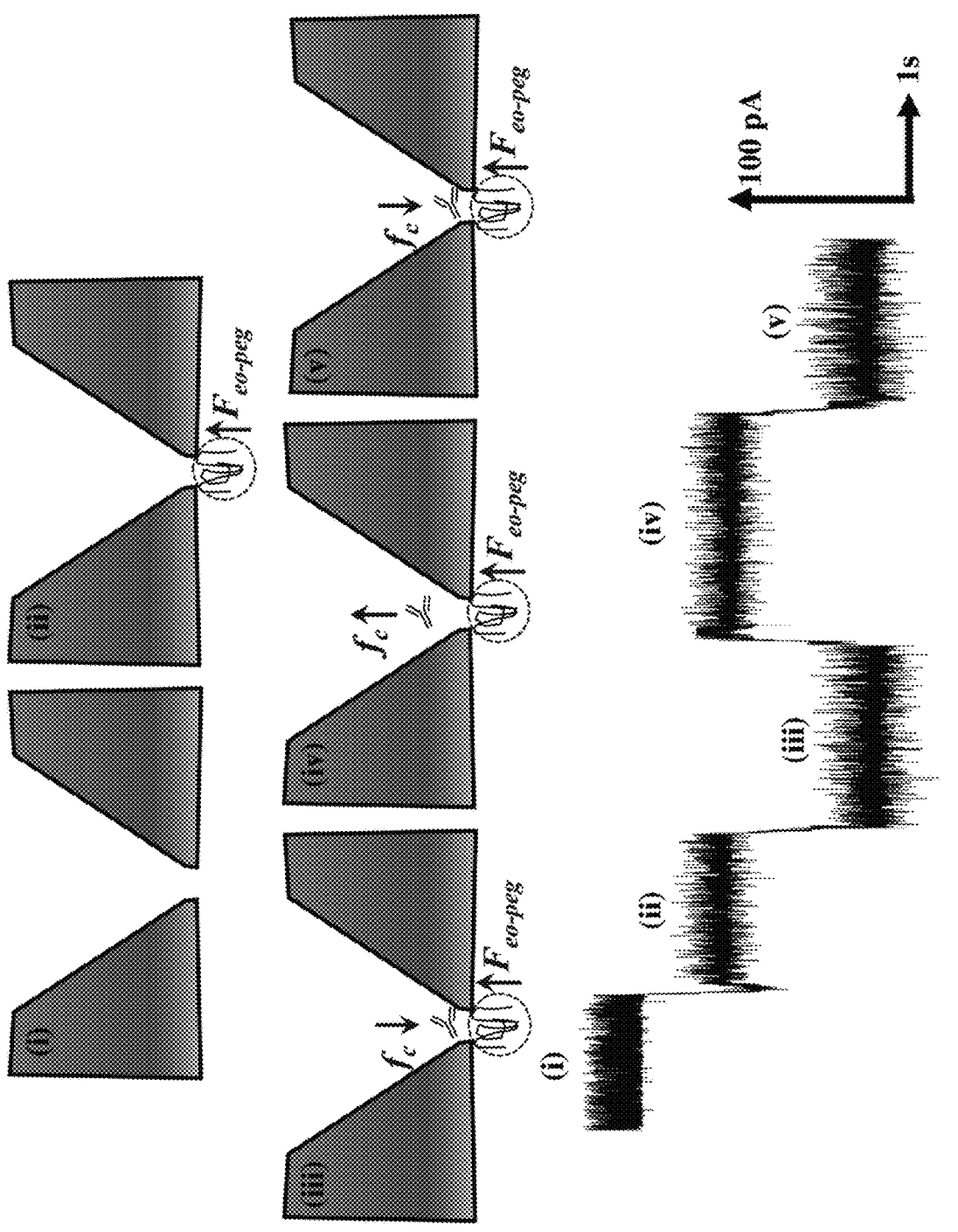
FIG. 10 shows reversible sensing signals of antibody measured with the reversibly trapping process: a nanopore provide the baseline current (i); a 60 kDa PEG is electroosmotically docked onto a nanopore (ii); a centrifugal force facilitates a molecule (i.e., antibody) translocating into.

To verify the direction-controlling function of the nanopore sensing device to molecular translocation according to an embodiment of the subject invention, the device was used for detecting chain-like molecules, such as PEG chains, and achieved a hundreds-of-times elongated molecular dwell time. The 10 kDa PEGs were tested while centrifugal forces with different directions exerted on them, as shown in FIGS. 8A-8C. While the direction of centrifugal forces is adjusted from normal to the nanopore to normal to the etched sidewall, the dwell time of the sensing signal was extended (from <100 msec to >200 msec), and the signal-to-noise ratio was optimized (from <1.5 to >4.5). Compared with conventional nanopore devices, such as protein nanopores, the inertial-kinetic method exhibited over one order of magnitude improvement on weight resolution (i.e., 0.1 kDa) in the measurement of PEGs.

Example 4—Selective Molecular Translocation

To confirm the capability of the nanopore sensing device according to an embodiment of the subject invention for selectively translocating and characterizing molecules, the device is used to detect the mixture of GFP-antibody conjugates, antibody, and GFP. The counter-balanced states of the three molecules were achieved by adjusting the illumination power to 60 mW (GFP-antibody conjugates), 75 mW (antibody), and 110 mW (GFP), respectively (see FIG. 9A-9D). Here electrokinetic forces exerted to the molecules trend to be balanced. Comparing the fingerprinting signals gotten in the different counter-balanced state of conjugates, antibody, and GFP, it was found that the majority of molecular inertial-kinetic translocation happened in the unique counter-balanced state of different molecules. Thus, the selectivity of molecular translocation was achieved by adjusting the strength of the electroosmotic effect of the nanopores through illumination intensity.

Example 5—Reversible Single-Molecule Sensing

To validate the reversible monitoring function of a nanopore sensing device according to an embodiment of the subject invention, the device was used for detecting the signal change related to distinct stages of molecular reversible motion into and out of the nanopore module 4, including (i) Voltage application across the nanopore module 4 establishes a baseline current. (ii) A charged and permeable nanostructure (i.e., 60 kDa PEG for a 15 nm nanopore) is driven to the nanopore 4 electro-kinetically for docking onto the nanopore 4 entrance thus closing off a nanocavity. (iii) A single molecule (i.e., antibody) can be trapped in the capped nanopore 4 by forward centrifugal force while the antibody is in the counter-balanced state. (iv) The single molecule can be driven out of the nanopore 4 again while the centrifugal force is changed to be reverse. (v) The single molecule can be trapped again in the nanopore 4 with the further adjustment of centrifugal force to forward. Thus, the reversible one-molecule sensing can be achieved by adjusting the direction of centrifugal force after the nanopore 4 is capped by a charged and permeable nanostructure.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A nanopore sensing device, comprising:
a centrifuge rotor (1);
a centrifuge tube (2); and
a nanopore module comprising single or multiple nanopores (4) located within the centrifuge tube (2),
wherein each nanopore (4) has radial asymmetry about a central axis.

2. A nanopore sensing device, comprising:
a centrifuge rotor (1);
a centrifuge tube (2);
a nanopore module comprising single or multiple nanopores (4) located within the centrifuge tube (2);
single or multiple flow cell modules (3) and (5) separated by the nanopores (4); and
a signal detection module (6) spanning the nanopore (4).

3. The nanopore sensing device of claim 2, comprising:
a signal amplifier module (7);
a control module (8); and
a wireless communication module (9).

4. The nanopore sensing device of claim 3, wherein the signal amplifier module (7), the control module (8), and the wireless communication module (9) are each, respectively, mounted within and configured and adapted to rotate with the centrifuge tube (2).

5. The nanopore sensing device of claim 4, wherein the centrifuge rotor (1) is configured and adapted to provide different rotation speed and direction to the centrifuge tube (2).

6. The nanopore sensing device of claim 4, wherein the signal detection module (6) spanning the nanopore module (4) is configured and adapted to provide different voltage potential.

7. The nanopore sensing device of claim 6, wherein the signal amplifier module (7) is configured and adapted to detect a sensing signal flowing over time across the detection module (6) spanning the nanopore module (4).

8. The nanopore sensing device of claim 7, wherein the control module (8) is configured and adapted to form a digital representation of the signal detected by the signal amplifier module (7).

9. A method for inertial-kinetic translocation and sensing of single molecules, the method comprising:

providing a nanopore sensing device, that comprises a nanopore, a driving circuit, a sensing circuit, and a communications device, each respectively located within a centrifuge tube;
applying, via the driving circuit, an electrical potential across the nanopore;
applying, via operation of the centrifuge tube, a centrifugal force across the nanopore;
driving through the nanopore, via inertial-kinetic translocation, a molecule to be measured; and
capturing, via the sensing circuit, a digital representation of a sensing signal across the nanopore over time.

10. The method according to claim 9, comprising:
transmitting, via the communications device, the digital representation of the sensing signal; and
receiving, at a location outside the centrifuge tube, the digital representation of the sensing signal.

11. The method according to claim 9, comprising:
extracting, from the digital representation of the sensing signal, a characteristic feature.

12. The method according to claim 11, wherein the characteristic feature is selected from the group consisting of an amplitude of a signal pulse amplitude; a dwell time of a signal pulse; a localized peak value in one of the foregoing; a mean, median, or standard deviation of a series of any of the foregoing; a decay time in any of the foregoing; a change in one of the foregoing; a difference between two of the foregoing; and a count of any of the foregoing.

13. The method according to claim 11, wherein the characteristic feature comprises a dwell time or a pulse amplitude.

14. The method according to claim 11, wherein the characteristic feature comprises a ratio of a second-peak amplitude to a first-peak amplitude.

15. The method according to claim 11, wherein the characteristic feature comprises a count of the number of peaks per molecule translocation.

16. A nanopore sensing device, comprising:
a centrifuge rotor (1);
a centrifuge tube (2);
a nanopore module consisting of single or multiple nanopores (4) located within the centrifuge tube (2);
single or multiple flow cell modules (3) and (5) separated by nanopore module (4);
a signal detection module (6) spanning the nanopore (4);
a signal amplifier module (7);
a control module (8); and
a wireless communication module (9);
wherein the signal amplifier module (7), the control module (8), and the wireless communication module (9) are each, respectively, mounted within and configured and adapted to rotate with the centrifuge tube (2);
wherein the centrifuge rotor (1) is configured and adapted to provide a rotation speed between 1,000 and 4,000 revolutions per minute (rpm) to the centrifuge tube (2);
wherein the nanopore structure is wide applicable;
wherein the nanopore has an adjustable pore size; and
wherein adjustable pore size is adjustable within a range of nanometers.

17. The nanopore sensing device of claim 16, wherein the signal detection module (6) spanning the nanopore module (4) is configured and adapted to provide a voltage potential between 0.3 volts (V) and 0.6 V;
wherein the preamplifier circuit board (7) is configured and adapted to detect a sensing signal flowing over time across the signal detection module (6) spanning the nanopore module (4); and wherein the microcontroller with the control module (8) is configured and adapted to form a digital representation of the sensing signal detected by the signal amplifier module (7).

\* \* \* \* \*